US007932059B2

(12) United States Patent
Westberry et al.

(10) Patent No.: US 7,932,059 B2
(45) Date of Patent: Apr. 26, 2011

(54) DUTP-BASED COMPOSITIONS FOR REDUCING PRIMER-AGGREGATE FORMATIONS DURING NUCLEIC ACID AMPLIFICATION

(75) Inventors: Ryan Smith Westberry, Westminster, CO (US); Lars-Erik Peters, Lafayette, CO (US); Jessica Jaclyn Greenlee, Lafayette, CO (US)

(73) Assignee: Qiagen North American Holdings, Valencia, CA (US)

( * ) Notice: Subject to any disclaimer, the term of this patent is extended or adjusted under 35 U.S.C. 154(b) by 0 days.

(21) Appl. No.: 10/588,689

(22) PCT Filed: Feb. 4, 2005

(86) PCT No.: PCT/US2005/003567
§ 371 (c)(1),
(2), (4) Date: Jun. 29, 2007

(87) PCT Pub. No.: WO2005/076925
PCT Pub. Date: Aug. 25, 2005

(65) Prior Publication Data
US 2007/0264633 A1    Nov. 15, 2007

Related U.S. Application Data

(60) Provisional application No. 60/541,999, filed on Feb. 4, 2004.

(51) Int. Cl.
*C12Q 1/68* (2006.01)
*C12P 19/34* (2006.01)
(52) U.S. Cl. ............... 435/91.2; 435/6; 435/91.1
(58) Field of Classification Search ............ None
See application file for complete search history.

(56) References Cited

U.S. PATENT DOCUMENTS

| | | | |
|---|---|---|---|
| 4,458,006 A | | 7/1984 | Donges et al. |
| 4,683,195 A | | 7/1987 | Mullis et al. |
| 4,683,202 A | | 7/1987 | Mullis et al. |
| 5,409,818 A | | 4/1995 | Davey et al. |
| 5,418,149 A | | 5/1995 | Gelfand et al. |
| 5,455,166 A | | 10/1995 | Walker |
| 5,536,649 A | * | 7/1996 | Fraiser et al. ............ 435/91.2 |
| 5,731,171 A | * | 3/1998 | Bohlander ............ 435/91.2 |
| 5,830,655 A | * | 11/1998 | Monforte et al. ............ 435/6 |
| 6,248,522 B1 | * | 6/2001 | Haberhausen et al. ............ 435/6 |
| 6,413,718 B1 | | 7/2002 | Leushner et al. |
| 6,783,940 B2 | * | 8/2004 | McLaughlin et al. ............ 435/6 |
| 2003/0073081 A1 | * | 4/2003 | Mukai et al. ............ 435/6 |

FOREIGN PATENT DOCUMENTS

| | | |
|---|---|---|
| WO | WO 02/090536 A2 | 11/2002 |
| WO | WO 03/040391 A2 | 5/2003 |

OTHER PUBLICATIONS

Carmody, M.W., et al., "Inhibition of DNA Hybridization Following Partial dUTP Substitution," Biotechniques, vol. 15, No. 4, pp. 692-694, 696 (1993).
Grace, M.B., et al., "Degradable dUMP Outer Primers in Merged Tandem (M/T)-nested PCT: Low and Single Copy DNA Target Amplification," Analytical Biochemistry, vol. 263, No. 1, pp. 85-92 (1998).
Rashtchian, A., et al., "Uracil DNA Glycosylase-Mediated Cloning of Polymerase Chain Reaction-Amplified DNA: Application to Genomic and cDNA Cloning." Analytical Biochemistry, vol. 206, No. 1, pp. 91-97 (1992).
Beaucage et al., "Deoxynucleoside Phosphoramidites—A New Class of Key Intermediates for Deoypolynucleotide Synthesis"; *Tetrahedon Letters*, 22:1859-1862 (1981).
Braasch and Corey, "Locke nucleic acid (LNA):fine tuning the recognition of DNA and RNA"; *Chem Biol* 2001, 8(1):1-7.
Maniatis et al., *Molecular Cloning: A Laboratory Manual* (New York: Cold Spring Harbor Laboratory) pp. 280-281 (1982).
Mok et al., The *Eschericha coli* Prerimosome and DnaB Helicase Can Form Replication Forks that Move at the Same Rate, *J. Biol. Chem.* 262:16558-16565 (1987).
Nielsen et al., "Peptide Nucleic Acid (PNA). A DNA Mimic with a Peptide Backbone", *Biconjug Chem.*, (1994) 5:3-7.
Radding, C.,"Homologous Pairing and Strand Exchange in Genetic Recombination"; *Ann. Review of Genetics*, 16:405-37 (1982).
Upretti, et al., "Enzyme leakage during cryopreservation of ram spermatoza"; *Animal Reproduction Science* 1996, vol. 41, pp. 27-36.
Vajda, T. Cryo-biorganic chemistry: molecular interactions at low temperatures. CMLS Cell Mol. Life Science 1999, vol. 41, pp. 27-36.
Yuzhakou et al., "Replisome Assembly Reveals the Basis for Asymmetric Function in Leading and Lagging Strand Replication", *Cell* 86:877-886, (1996).

* cited by examiner

Primary Examiner — Young J Kim
(74) Attorney, Agent, or Firm — Todd Lorenz; Arnold & Porter LLP

(57) ABSTRACT

Methods and compositions are provided for enhanced specificity and sensitivity of amplification reaction mixtures. Compositions in accordance with the present invention provide for reduced formation of primer-aggregates during amplification reactions. Reaction mixes include dNTPs, where a portion of the dNTPs has been replaced with an unconventional nucleotide, e.g., dUTP. Unconventional nucleotide concentrations are typically between 10% to 50% of the concentration of one of the standard dNTP. In some compositions the unconventional nucleotide is dUTP which replaces from about 10% to about 50% of the dTTP in the dNTP mix.

24 Claims, 13 Drawing Sheets

Protocol
Cycle 1: (1X)
    Step 1:    95.0C    for 01:00
Cycle 2: (40X)
    Step 1:    95.0C    for 00:20
    Step 2:    53.0C    for 00:20
    Step 3:    68.0C    for 00:20
Cycle 3: (1X)

| HotMaster Taq Reactions w/ STND dNTPs | | |
|---|---|---|
| Reaction Component | Initial Concentration or Volume | Final Concentration/Volume |
| QuantMaster Probe Buffer | 10X | 1X |
| dNTP Mix | | |
| dATP | 10mM | 200uM |
| dCTP | 10mM | 200uM |
| dGTP | 10mM | 200uM |
| dTTP | 10mM | 200uM |
| FactorVIII Forward Primer | 10uM | 200nM |
| FactorVIII Reverse Primer | 10uM | 200nM |
| HotMaster Taq Polymerase | 5U/ul | 1U |
| MBGW | N/A | 36.8 - 38.8 uL |
| *Human gDNA (Promega) | 25ng/uL | 50ng |
| * Not Included in NTCs | | |

| HotMaster Taq Reactions w/ 20% dUTP Mix | | |
|---|---|---|
| Reaction Component | Initial Concentration or Volume | Final Concentration/Volume |
| QuantMaster Probe Buffer | 10X | 1X |
| dNTP Mix | | |
| dATP | 10mM | 200uM |
| dCTP | 10mM | 200uM |
| dGTP | 10mM | 200uM |
| dTTP | 8mM | 160uM |
| dUTP | 2mM | 40uM |
| FactorVII Forward Primer | 10uM | 200nM |
| FactorVIII Reverse Primer | 10uM | 200nM |
| HotMaster Taq Polymerase | 5U/ul | 1U |
| MBGW | N/A | 36.8 - 38.8 uL |
| *Human gDNA (Promega) | 25ng/uL | 50ng |
| * Not Included in NTCs | | |

*FIG. 2B*

Beta-Actin mRNA Sequence atggatgatgatatcgccgcgctcgtcgtcgacaacggctccggcatgtgcaaggccggcttcgcgggcga
cgatgccccggccgcgcgttctcccctccatcgtggggcgccccaggcaccagggcgtgatggtgggcatg
ggtcagaaggattcctatgtgggcgacgaggcccagagcaagagaggcatcctcaccctgaagtaccca
tcgagcacggcatcgtcaccaactgggacgacatggagaaaatctggaaccttctacaatgagctg
cgtgtggctcccgaggagcaccccgtgctgctgaccgaggcccctgaaccccaaggccaaccgcga
gaagatgaccca

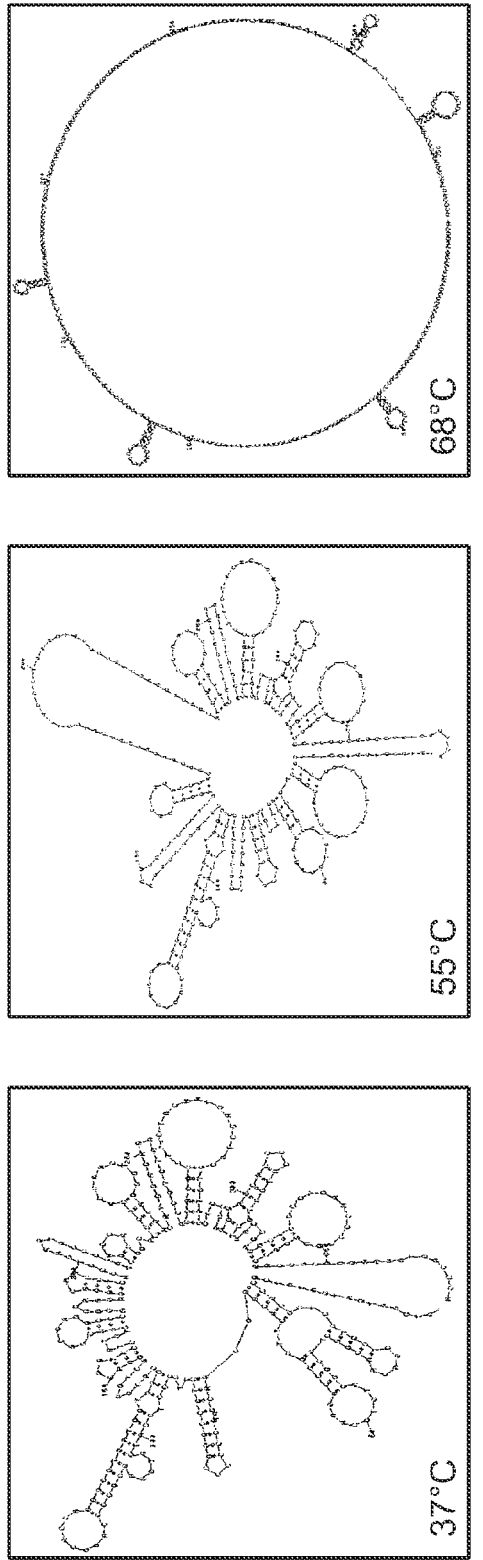

FIG. 5A

Beta-Actin Partial Gene Sequence w/ Intron atggatgatgatatcgccgcgctcgtcgtcgacaacggctccggcatgtgcaaggccggcttcgcgggcga
cgatgccccccgggccgtcttccctccatcgtggggcgccccaggcaccag|gtagggagctggctgg
gtggggcagccccgggagcggggccaaggcgcgtttctctgcacaggagcctccccgtttccgg
ggtggctgccgccgcctcaggcttcttgtcctttcccag|ggcgtgatggtgggcatggtcagaa
ggattcctatgtgggcgacgaggcccagagcaagagagagcatcctcacctgaatcctcacctgagcac
ggcatcgtcaccaactgggacgacatggagaaaatctggcaccacaccttctacaatgagctgcgtgtggct
cccgaggagcaccccgtgctgctgaccgaggcccaaggccaaccgcgagaagatga
ccca

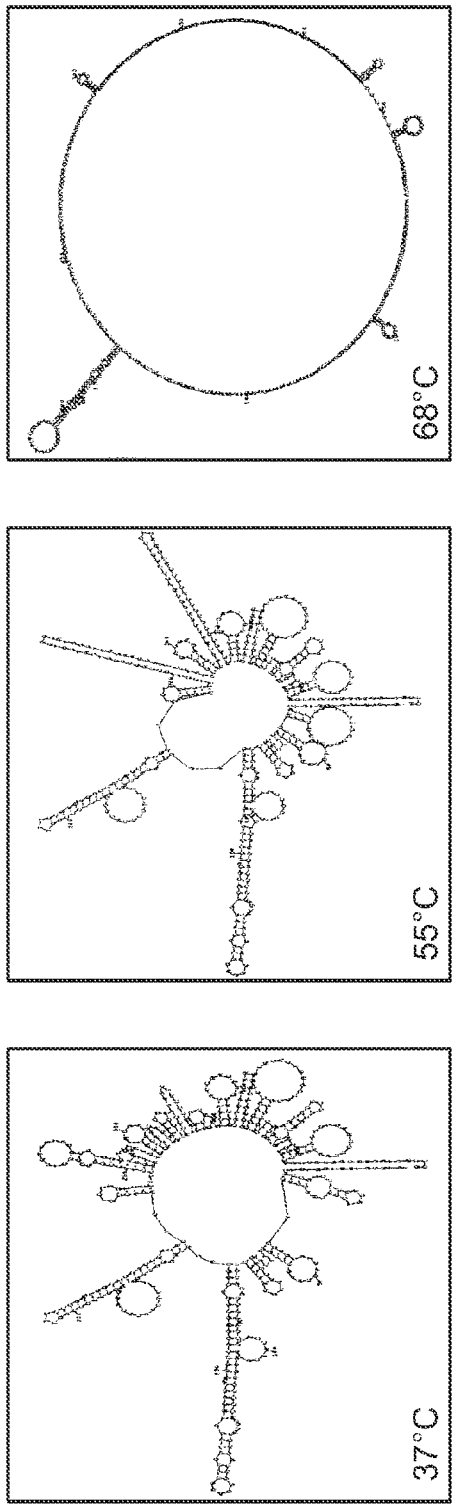

FIG. 5B

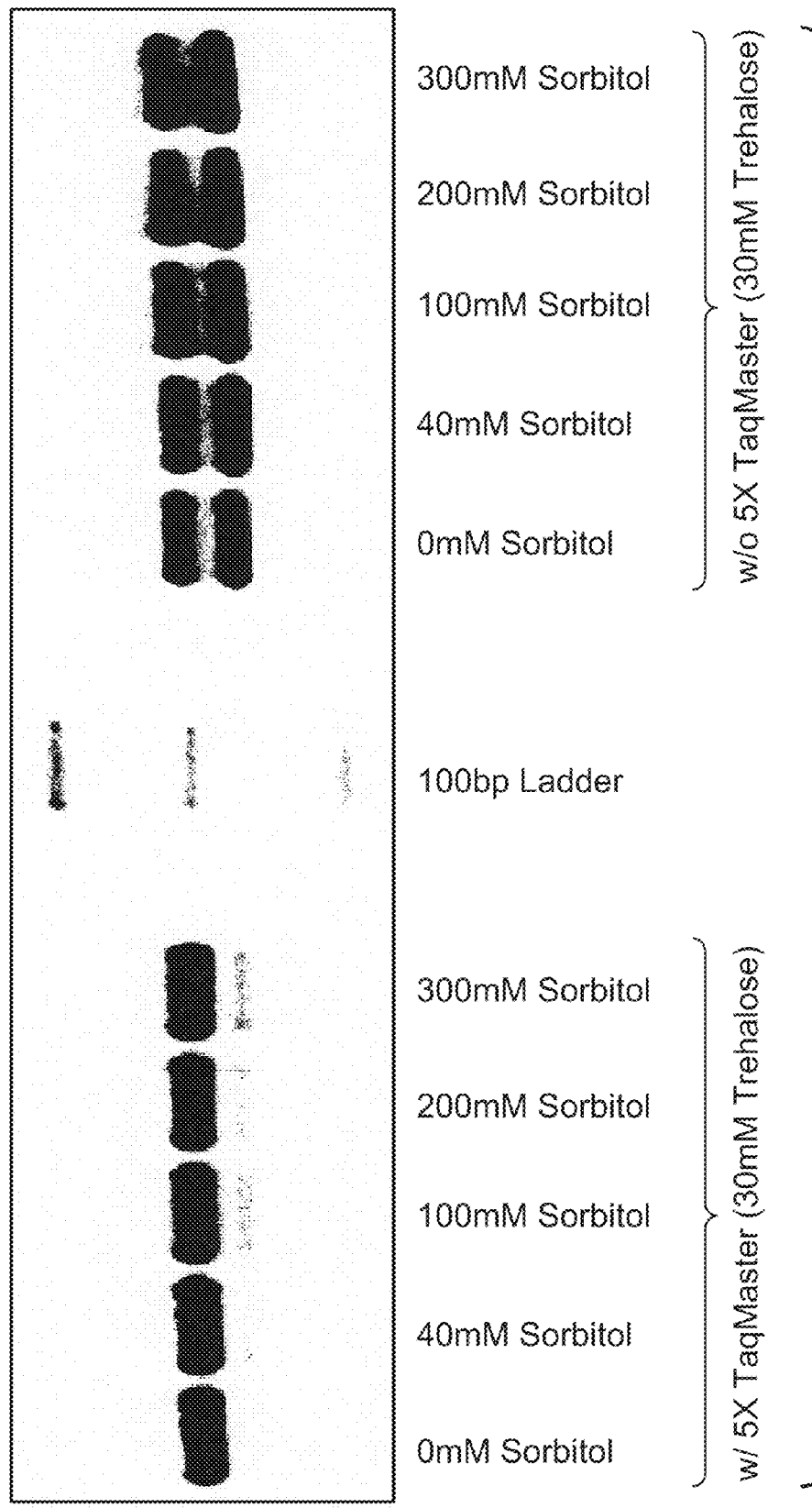

DUTP-BASED COMPOSITIONS FOR REDUCING PRIMER-AGGREGATE FORMATIONS DURING NUCLEIC ACID AMPLIFICATION

CROSS-REFERENCE TO RELATED APPLICATIONS

This application is a 371 of PCT/US05/03567, filed on Feb. 4, 2005, which claims priority to U.S. Provisional Patent Application No. 60/541,999 titled "METHODS AND COMPOSITIONS TO ENHANCE AMPLIFICATION EFFICIENCY AND SIGNAL," filed Feb. 4, 2004, which is hereby incorporated by reference herein.

FIELD OF THE INVENTION

The invention generally relates to methods and compositions for increasing the specificity and sensitivity of nucleic acid amplification reactions, and more particularly, relates to methods and compositions for reducing the tendency of primers involved in amplification reactions to non-specifically anneal with each other and form primer aggregates.

BACKGROUND OF THE INVENTION

The ability to prepare large amounts of nucleic acid molecules is requisite to a number of protocols in molecular biology, as well as a basic requirement in numerous downstream uses in biotechnology and clinical research. For example, amplified nucleic acid molecules are often used in cloning experiments, DNA sequencing reactions, restriction digestion reactions, and subsequent ligation reactions, and these uses are all, or to some extent, dependent on the quality and quantity of the starting DNA material. As such, there has been, and continues to be, a need for reliable methods for preparing large amounts of quality, sequence-specific nucleic acid molecules.

In addition, the ability to detect and/or quantify nucleic acid molecules from a mixed starting material is useful in a number of clinical, industrial and basic research applications. For example, sensitive and accurate detection and quantification of viral nucleic acid sequences in a patient sample is helpful in a clinical setting for accurate diagnosis and subsequent treatment of a patient. Such detection and quantification processes generally require amplification of one or more target nucleic acid molecules present in the starting material. As such, there has been, and continues to be, a need for facilitating the detection and quantification of target nucleic acid sequences from a starting material, which again requires reliable methods for preparing large amounts of quality, sequence-specific nucleic acid molecules.

The predominant approach for amplifying nucleic acid is via the polymerase chain reaction (PCR). PCR is a convenient in vitro amplification process useful in the exponential increase of template nucleic acid. One of the more critical facets of a successful PCR reaction is primer design, requiring specific primers that hybridize to the target template sequence. However, there is a relatively narrow range of reaction conditions (temperature, ion concentration, denaturing agents, etc.) where a primer will specifically anneal to its complementary target. Moreover, even with optimal primer selection, many PCR reactions produce little or no product due to non-specific amplification and/or primer aggregation.

Primer aggregation typically results from the extension of one primer off of the other primer in the PCR reaction, i.e., one primer acts as a template for the other primer; this process occurs even though no stable annealing of the primer is accomplished. Typically, as primers begin to form aggregates within a PCR reaction, the aggregates become valid templates for efficient PCR amplification, since the primer aggregates contain both primer annealing sites. In this manner, primer aggregation has a persistent and detrimental effect on PCR reactions, as each primer-aggregate acts as a template for additional rounds of non-specific amplification. Since the generation of primer aggregation is a major problem at low temperatures during the amplification reaction, i.e., prior to thermocycling, primer aggregation has typically been addressed using "hot start" technologies. Additional technologies for addressing this problem, however, are needed, as even "hot start" technologies are only partially successful in their approach to limiting primer aggregation. In addition, even small increases in non-specific amplification can lead to significant losses in sensitivity and specificity during a PCR or other like nucleic acid amplification reaction.

As such, there is a continuing need in the art for improvement of PCR techniques and compositions that allow for a reduction in primer aggregation during nucleic acid amplification reactions, and in particular PCR.

SUMMARY OF THE RELEVANT LITERATURE

Over the past ten to fifteen years, the nucleotide deoxyuridine triphosphate (dUTP) has been employed in conjunction with uracil DNA glycosylase (UDG or UNG) in amplification reactions as a general methodology for reducing contamination, wherein dUTP conventionally replaces thymidine triphosphate (TTP) in the amplification reaction mixture. U.S. Pat. No. 5,418,149 discloses the use of dUTP for inactivating contaminating amplicons in PCR by generally distinguishing previously produced amplicons, those that incorporate uracil, from new target sequences, i.e., template sequences, that do not contain uracil. The uracil-containing DNA is treated with uracil DNA glycosylase (UDG or UNG) to remove uracil, leaving the sugar-phosphodiester backbone intact, i.e., the UDG treated backbone having abasic sites. These abasic sites are susceptible to hydrolysis by heat or alkali, thereby fragmenting the uracil-containing DNA and rendering it unamplifiable during subsequent amplification reactions. The elevated heat or alkali also results in inactivation of the UDG. Large excesses of dUTP are required for this application, typically being added at concentrations well above concentrations normally used for conventional dNTPs.

A variation of this "clean-up" method has been described in U.S. Pat. No. 5,536,649 ('649), for clean-up or inactivation of amplicons during strand displacement amplification reactions (SDA). dUTP is incorporated into amplicons produced by amplification reactions using SDA. Amplicons having incorporated uracil nucleotides are treated with UDG, and the UDG is inactivated by inclusion of the UDG inhibitor protein Ugi. Note that large concentrations of dUTP are required for this increase in SDA amplification efficiency, i.e., 0.5 mM to 4 mM. dUTP has also been used in methods for targeting DNA that has been sequenced, as described in U.S. Pat. No. 6,413,718. As with the above-described amplification reactions, dUTP is incorporated into sequenced product and then degraded at the end of the reactions to eliminate contamination problems.

In general, therefore, dUTP incorporation is uniformly combined in the art with an enzymatic degradation step employing UNG or other like enzyme, to degrade uracil-containing amplicons. Moreover, the dUTP will typically completely replace one of the naturally-occurring nucleotide triphosphates in the reaction mixture, usually at a concentration well in excess of any one of the three remaining conventional nucleotides.

SUMMARY OF THE INVENTION

The present invention provides compositions and methods for improving the sensitivity and specificity of nucleic acid amplification reactions, such amplification reactions typically comprising at least one cycle of a denaturation step, an annealing step, and an extension step. Compositions and methods of the present invention substitute deoxyuridine triphosphate (dUTP) for a portion of deoxythymidine triphosphate (dTTP) in a reaction mixture containing all four conventional nucleotides. As demonstrated herein for the first time, the replacement of only a portion of dTTP with dUTP reduces primer aggregation and, therefore, non-specific amplification, over the course of an amplification reaction. In addition, other unconventional nucleotides such as, e.g., dITP, can be included with dUTP in the reaction mixture to replace a portion of other conventional nucleotides.

In one aspect, methods and compositions for inhibiting primer aggregate formation in a nucleic acid amplification reaction are provided, comprising the addition of dUTP to an amplification reaction mixture containing each of dTTP, dATP, dCPT and dGTP. In preferred embodiments, at least 10% and up to 75% of the dTTP in a standard dNTP mix is replaced with dUTP and the modified dNTP mixture is then used in the amplification reaction. Compositions in accordance with this embodiment include dNTP mixtures having 5, 10, 25, 40, 50, 60, 70 or 75% of the dTTP replaced by dUTP. Typically, each reaction will include from about 20 µM to about 300 µM dUTP in a standard dNTP mix, wherein the concentration of dUTP preferably does not exceed 75% of the concentration of any one starting conventional nucleotide, with the combined concentration of dUTP and dTTP similar to the concentration of the other dNTPs. As such, an embodiment of the present invention can include, for example, 25% dUTP/75% dTTP, 50% dUTP/50% dTTP, 75% dUTP/25% dTTP and 100% of each of the other four conventional nucleotides. Note also that other unconventional nucleotides can be combined with the dUTP to make up the dUTP-based fraction, provided again that the upper limit of 75% unconventional nucleotide is not exceeded. As demonstrated herein, amounts that exceed this concentration have deleterious effects on the yield of the reaction.

In another aspect, primers are designed having one or more base analogs incorporated therein for the inhibition of primer-aggregation and other non-specific amplification reactions during a nucleic acid amplification reaction. In general, these base analogs derive from the unconventional nucleotides. In preferred embodiments, the base analog is uracil, which replaces thymidine bases. In this embodiment, the uracil maintains the base pairing specificity of thymidine.

The present invention further provides improved nucleic acid amplification reaction mixtures for use in nucleic acid amplification reactions, comprising a combination of a polyol, an anti-freeze protein and a dNTP mix that includes a ratio of dUTP:dTTP. In a preferred embodiment, one or more of these enhancers are added to a reaction mixture comprising a zwitterionic buffer. As detailed herein, these novel reaction mixture components may improve amplicon yield as well as signal intensity in quantification reactions, and enhance sensitivity of the amplification reaction.

BRIEF DESCRIPTION OF THE DRAWINGS

FIGS. 5A and 5B graphically show the Beta-Actin sequence used for the sorbitol secondary structure assays. FIG. 5A shows the secondary structure of the gene (SEQ ID NO: 1) at 37, 55 and 68° C. in the absence of a extremely GC rich region, and FIG. 5B shows the same gene with the included GC rich region (SEQ ID NO: 2) that promotes secondary structure even at 37, 55 and 68° C.

FIGS. 7A and 7B are as above in FIG. 6, except PCR was performed in a combination of several chemical agents, including sorbitol, mannitol, dUTP, DMSO, single-stranded binding protein and trehalose.

DETAILED DESCRIPTION OF THE INVENTION

Figure 1:
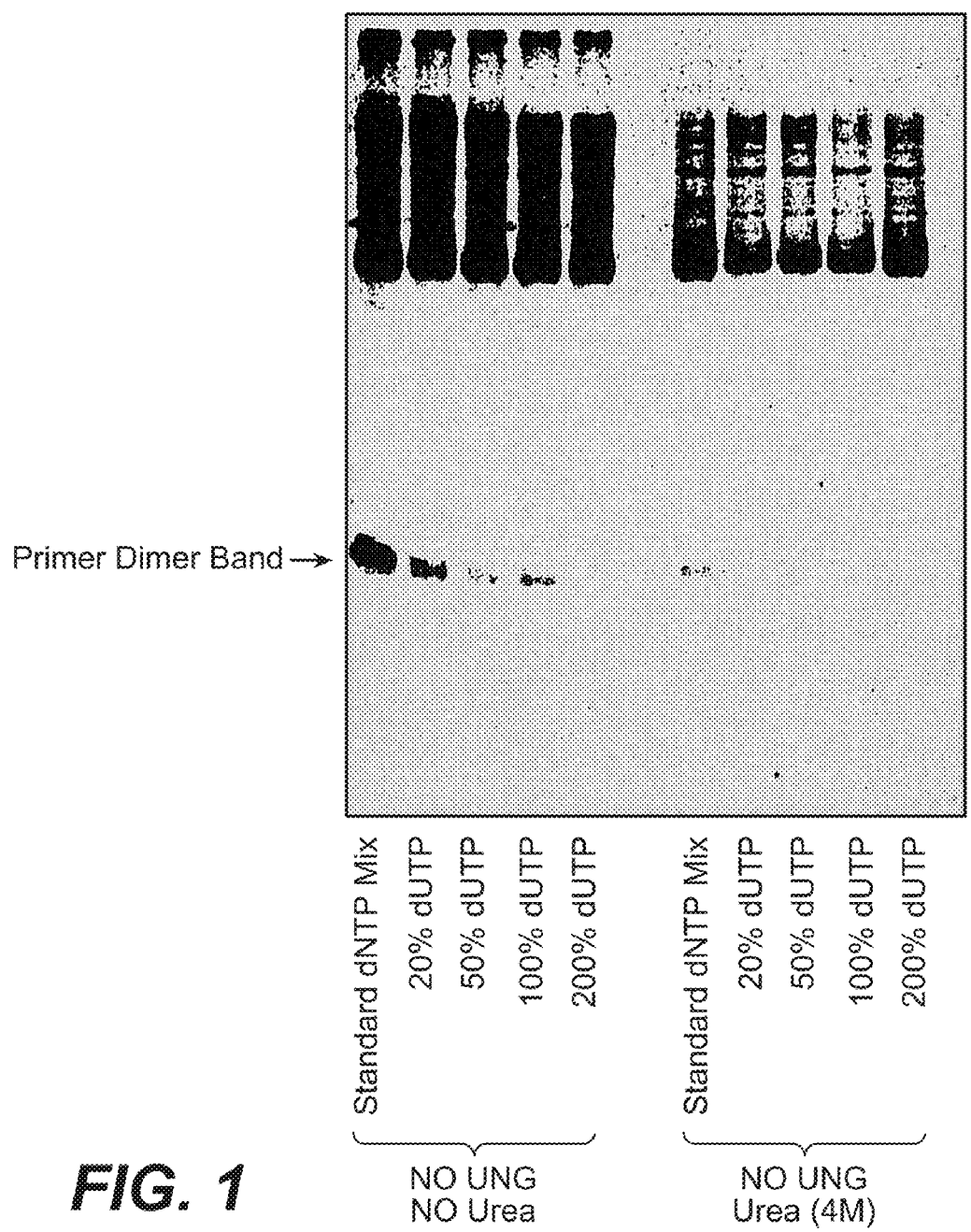
FIG. 1 is a stained 1% agarose gel showing the reaction products from PCR where varying percentages of dTTP in the dNTPs was replaced with dUTP. The incorporation of dUTP into the reaction mixes significantly reduces the amount of primer-dimer formed during each reaction.

The following definitions are provided to facilitate understanding of certain terms used frequently herein and are not meant to limit the scope of the present disclosure:

As used herein, "amplification reaction" or "nucleic acid amplification reaction" refers to any in vitro method for increasing the number of copies of a desired nucleic acid sequence with the use of a DNA polymerase. Nucleic acid amplification reactions include, for example, the polymerase chain reaction (PCR) (as described in U.S. Pat. Nos. 4,683, 195 and 4,683,202, which are hereby incorporated by reference), Nucleic Acid Sequence-Based Amplification (NASBA) (as described in U.S. Pat. No. 5,409,818, which is hereby incorporated by reference) and Strand Displacement Amplification (SDA) (as described in U.S. Pat. No. 5,455, 166, which is hereby incorporated by reference). As is well known in the art, such reactions find advantageous use in numerous nucleic acid detection methods for determining the presence of one or more target nucleic acid sequences in a sample, as well as in a wide variety of nucleic acid quantification methods for quantifying the amount of amplicon(s) produced by the reaction.

As used herein, "antisense" refers to polynucleotide sequences that are complementary to target "sense" polynucleotide sequences.

As used herein, "carrier protein(s)" refers to Bovine Serum Albumin (BSA), Prionex, Single Stranded Binding Protein (SSB), Cold Water Fish Gelatin, gelatin, Gro L, Gro S, DNAK, Heat Shock Protein 70 (HSP70), Apolipoprotein, as well as other like serum albumins.

As used herein, "Ct shift" or "threshold cycle" refers to the cycle at which an amplification product is detectable, a Ct shift of 1.5 to 3 cycles is equivalent to an approximate 5 to 10 fold higher input amount of template DNA.

As used herein, "nucleic acid" or "NA" refers to both a deoxyribonucleic acid (DNA) and a ribonucleic acid (RNA), as well as modified and/or functionalized versions thereof. Similarly, the term "nucleotide" as used herein includes both individual units of ribonucleic acid and deoxyribonucleic acid as well as nucleoside and nucleotide analogs, and modified nucleotides such as labeled nucleotides. In addition, "nucleotide" includes non-naturally occurring analog structures, such as those in which the sugar, phosphate, and/or base units are absent or replaced by other chemical structures. Thus, the term "nucleotide" encompasses individual peptide nucleic acid (PNA) (Nielsen et al., Bioconjug. Chem. 1994; 5(1):3-7) and locked nucleic acid (LNA) (Braasch and Corey, Chem. Biol. 2001; 8(1):1-7) units.

As used herein, "conventional nucleotides" refers to nucleotides which naturally occur in a particular nucleic acid, e.g., ATP, TTP, CTP and GTP are conventional nucleotides in DNA. For purposes of the present invention conventional nucleotides also includes deoxynucleotides, e.g., dATP, dTTP, dCTP, and dGTP.

As used herein, "unconventional nucleotide" refers to a nucleotide that is not naturally occurring in a particular nucleic acid. Unconventional nucleotides may be naturally-occurring nucleotides, e.g., hypoxanthine, or they may be chemically-modified derivatives or analogs of conventional nucleotides, e.g., N-7-methylguanine, deoxyuridine and deoxy-3'-methyladenosine. For example, uracil is a naturally occurring and conventional nucleotide in RNA but is unconventional in DNA. Unconventional nucleotides includes deoxynucleotides, e.g., dUTP, dITP, and the like. Other unconventional nucleotides include ITP and deaza-dGTP.

As used herein, "polynucleotide," "oligonucleotide" or grammatical equivalents thereof means at least two nucleotides covalently linked together. As will be appreciated by those of skill in the art, various modifications of the sugar-phosphate backbone may be done to increase the stability of such molecules in physiological environments, including chemical modification such as, e.g., phosphorothioate or methyl phosphonate. Further, such molecules may be functionalized by coupling with one or more molecules having distinct characteristic properties for purposes of, e.g., facilitating the addition of labels.

As used herein, "primer aggregate(s)" refers to non-specific interactions (for example annealing or other like interactions) between two or more primer molecules during an amplification reaction. Primer aggregate formation leads to a reduction in the effective primer concentration during an amplification reaction and to an increase in non-specific product buildup that lowers overall reaction sensitivity and specificity. Primer aggregates include, but are not limited to, primer-dimers, primer-trimers, hairpins, fill-ins, direct hybrids, and the like.

As used herein, "nucleic acid sequence" refers to the order or sequence of nucleotides along a strand of nucleic acids. In some cases, the order of these nucleotides may determine the order of the amino acids along a corresponding polypeptide chain. The nucleic acid sequence thus codes for the amino acid sequence. The nucleic acid sequence may be single-stranded or double-stranded, as specified, or contain portions of both double-stranded and single-stranded sequences. The nucleic acid sequence may be composed of DNA, both genomic and cDNA, RNA, or a hybrid, where the sequence comprises any combination of deoxyribo- and ribo-nucleotides, and any combination of bases, including uracil (U), adenine (A), thymine (T), cytosine (C), guanine (G), inosine, xathanine hypoxathanine, isocytosine, isoguanine, etc.

As used herein, "complementary" or "complementarity" refers to the ability of a nucleotide in a polynucleotide molecule to form a base pair with another nucleotide in a second polynucleotide molecule. For example, the sequence 5'-A-C-T-3' is complementary to the sequence 3'-T-G-A-5'. Complementarity may be partial, in which only some of the nucleotides match according to base pairing, or complete, where all the nucleotides match according to base pairing. For purposes of the present invention "substantially complementary" refers to 95% or greater identity over the length of the target base pair region.

As used herein, "isolated" and "purified" for purposes of the present invention are interchangeable, and refer to a polynucleotide, for example a target nucleic acid sequence, that has been separated from cellular debris, for example, high molecular weight DNA, RNA and protein. This would include an isolated RNA sample that would be separated from cellular debris, including DNA.

As used herein, "protein," "peptide," and "polypeptide" are used interchangeably to denote an amino acid polymer or a set of two or more interacting or bound amino acid polymers.

As used herein, "real-time PCR" refers to quantitative PCR techniques that typically use fluorescence probes, beacons, and/or intercalating dyes during all cycles of the process.

As used herein, "stringency" refers to the conditions, i.e., temperature, ionic strength, solvents, and the like, under which hybridization between polynucleotides occurs. Hybridization being the process that occurs between the primer and template DNA during the annealing step of the amplification process.

Embodiments of the present invention provide methods and compositions for reducing primer aggregation during a nucleic acid amplification reaction, i.e., primer-based nucleic acid amplification. Reduction of primer aggregation has the dual effect of making primer-based amplification reactions more sensitive and specific and can result in enhanced product yield. Embodiments of the present invention include at least the following:

Replacement of a portion of dTTP in a conventional dNTP mix in a primer-based amplification reaction with dUTP. Embodiments reduce the formation of primer aggregates during the amplification reaction.

Replacement of a portion of dTTP in a conventional dNTP mix in a primer-based amplification reaction with a combination of dUTP and at least one more unconventional nucleotide, for example dITP or deaza-dGTP. Note that this embodiment is most useful where incorporation of mutations into the amplicon is not a major issue, given that incorporation of ITP, or other non-dUTP like unconventional bases, into an amplicon can cause high mutation rates in the product, i.e., amplification reactions that focus on detection of a product and not the use or sequencing of the product are most preferred for this embodiment Design of primers are provided that incorporate one or more uracils throughout the length of the primer to reduce the potential for formation of primer aggregates during amplification reactions.

Inclusion of dUTP, sorbitol, or other like polyol, and AFP in a zwitterionic buffer formulation, i.e., TAPs-tris KCL or TAPS-KOH KCL, to provide a high performance amplification reaction mix (increases sensitivity, specificity, signal size and storage stability), especially where the pH is between 7.9 and 8.1.

Nucleic Acid Amplification

In one aspect, the invention provides methods for amplifying a nucleic acid molecule, comprising subjecting the nucleic acid molecule to an amplification reaction in amplification reaction mixture. The amplification reaction mixture having up to 75% of dTTP of a standard dNTP mix replaced with dUTP. In preferred embodiments the dTTP is replaced with dUTP, however, it should be understood that the scope of the invention includes replacement of some portion of the dUTP with other unconventional nucleotides. Typically, final reaction mixture concentrations of the dUTP, or other like unconventional nucleotide, are from about 20 μM to about 300 μM, preferably between 20 μM to 160 μM, when the standard dNTP concentration is about 200 μM to 400 μM. Typically, the percent of dUTP to dTTP is about 10% to about 75%, i.e., about 10% to 75% of dTTP can be replaced with dUTP.

In an alternative embodiment, primers useful in the amplification reaction, appropriate for the target nucleic acid, are designed with one or more uracil bases in replacement of one or more corresponding thymidine bases. The uracil bases may be located anywhere throughout the primer sequence where a thymidine base is located. Note that uracil is the preferred replacement base due to its specificity to base pairing within a DNA molecule.

Nucleic acid molecules may be amplified according to any of the literature-described manual or automated amplification methods. Nucleic acid amplification results in the incorporation of nucleotides into a DNA molecule or primer, thereby forming a new DNA molecule complementary to a nucleic acid template. The formed DNA molecule and its template can be used as templates to synthesize additional DNA molecules. As used herein, one amplification reaction may consist of many rounds of DNA replication. DNA amplification reactions include, for example, polymerase chain reactions ("PCR"). One PCR reaction may consist of 10 to 100 "cycles" of denaturation and synthesis of a DNA molecule. Such methods include, but are not limited to PCR (as described in U.S. Pat. Nos. 4,683,195 and 4,683,202, which are hereby incorporated by reference), Strand Displacement Amplification) ("SDA") (as described in U.S. Pat. No. 5,455,166, which is hereby incorporated by reference), and Nucleic Acid Sequence-Based Amplification ("NASBA" (as described in U.S. Pat. No. 5,409,818, which is hereby incorporated by reference). For example, amplification may be achieved by a rolling circle replication system which may even use a helicase for enhanced efficiency in DNA melting without heat (See Yuzhakou et al., "Replisome Assembly Reveals the Basis for Asymmetric Function in Leading and Lagging Strand Replication," Cell 86:877-886 (1996) and Mok et al., "The *Escherichia coli* Preprimosome and DnaB Helicase Can Form Replication Forks That Move at the Same Rate," J. Biol. Chem. 262:16558-16565 (1987), which are hereby incorporated by reference). Most preferably, nucleic acid molecules are amplified by the methods of the present invention using PCR-based amplification techniques.

In a preferred embodiment, the amplification reaction involves a high temperature denaturation step. Preferred temperatures for the high temperature denaturation step range from about 90° C. to about 98° C., with temperatures from 93° C. to 94° C. being especially preferred. Such preferred amplification reactions include thermocycling amplification reactions, such as polymerase chain reactions involving from about 10 to 100 cycles, more preferably from about 25 to 50 cycles, and peak temperatures of from about 93° C. to about 94° C.

In a preferred embodiment, a PCR reaction is done using a polymerase produced exponential quantities relative to the number of reaction steps involved, at lease one specific nucleic acid sequence, given (a) that the ends of the required sequence are known in sufficient detail that oligonucleotides can be synthesized which will hybridize to them and (b) that a small amount of the sequence is available to initiate the chain reaction. The product of the chain reaction will be discrete nucleic acid duplex with termini corresponding to the ends of the specific primers employed.

Any source of nucleic acid, in purified or nonpurified form, can be utilized as the starting nucleic acid, provided it contains the specific nucleic acid sequence desired. Thus, the process may employ, for example, DNA or RNA, including messenger RNA, which DNA or RNA may be single stranded or double stranded. In addition, a DNA-RNA hybrid which contains one strand of each may be utilized. A mixture of any of these nucleic acids may also be employed, or the nucleic acids produced from a previous amplification reaction herein using the same or different primers may be so utilized. The nucleic acid amplified is preferably DNA. The specific nucleic acid sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the β-globin gene contained in whole human DNA or a portion of nucleic acid sequence due to a particular microorganism which organism might constitute only a very minor fraction of a particular biological sample. The starting nucleic acid may contain more than one desired specific nucleic acid sequence which may be the same or different. Therefore, the method is useful not only for producing large amounts of one specific nucleic acid sequence, but also for amplifying simultaneously more than one different specific nucleic acid sequence located on the same or different nucleic acid molecules.

The nucleic acid or acids may be obtained from any source and include plasmids and cloned DNA or RNA, as well as DNA or RNA from any source, including bacteria, yeast, viruses, and higher organisms such as plants or animals. DNA or RNA may be extracted from blood, tissue material such as corionic villi or amniotic cells by a variety of techniques such as that described by Maniatis et al., Molecular Cloning: A Laboratory Manual, (New York: Cold Spring Harbor Laboratory) pp 280-281 (1982).

Any specific nucleic acid sequence can be produced by the present methods. It is only necessary that a sufficient number of bases at both ends of the sequence be know in sufficient detail so that two oligonucleotide primers can be prepared which hybridize to different strands of the desired sequence and at relative positions along the sequence such that an extension product synthesized from one primer, when it is separated from its template (complement), can serve as a template for extension of the other primer into a nucleic acid of defined length. The greater the knowledge about the bases at both ends of the sequence, the greater the specificity of the primers for the target nucleic acid sequence, and, thus, the greater the efficiency of the process. It will be understood that the work primer as used hereinafter may refer to more than one primer, particularly in the case where there is some ambiguity in the formation regarding the terminal sequence(s) of the fragment to be amplified. For instance, in the case where a nucleic acid sequence is inferred from protein sequence information a collection of primers containing sequences representing all possible codon variations based on degeneracy of the genetic code can be used for each strand. One primer from this collection will be homologous with the end of the desired sequence to be amplified.

Oligonucleotide primers may be prepared using any suitable method, such as, for example, the phosphotriester and phosphodiester methods or automated embodiments thereof. In one such automated embodiment diethylophosphoramidites are used as starting materials and may be synthesized as described by Beaucage et al., Tetrahedron Letters, 22:1859-1862 (1981), which is hereby incorporated by reference. One method for synthesizing oligonucleotides on a modified solid support is described in U.S. Pat. No. 4,458,006, which is hereby incorporated by reference. It is also possible to use a primer which has been isolated from a biological source (such as a restriction endonuclease digest).

As noted above, in one embodiment oligonucleotide primers are designed to incorporate uracil bases instead of thymidine bases. The addition of uracil lowers the melting temperature of the primer-template interaction, thereby lowering the potential for primers to interact and form primer-aggregates.

The specific nucleic acid sequence is produced by using the nucleic acid containing that sequence as a template. If the nucleic acid contains two strands, it is necessary to separate the strands of the nucleic acid before it can be used as the template, either as a separate step or simultaneously with the synthesis of the primer extension products. This strand separation can be accomplished by any suitable denaturing method including physical, chemical, or enzymatic means. One physical method of separating the strands of the nucleic acid involves heating the nucleic acid until it is completely (>99%) denatured. Typical heat denaturation may involve temperatures ranging from about 80° C. to 105° C. for times ranging from 1 to 10 minutes. Strand separation may also be induced by an enzyme from the class of enzymes known as helicases or the enzyme RecA, which has helicase activity and is known to denature DNA. The reaction conditions suitable for separating the strands of nucleic acids with helicases are described by Colg Spring Harbor Symposia on Quantitative Biology, Vol. XLIII "DNA: Replication and Recombination" (New York: Cold Spring Harbor Laboratory, 1978), and techniques for using RecA are reviewed in C. Radding, Ann, Rev. Genetics, 16:405-37 (1982), which is hereby incorporated by reference.

If the original nucleic acid containing the sequence to be amplified is single stranded, its complement is synthesized by adding one or two oligonucleotide primers thereto. If an appropriate single primer is added, a primer extension product is synthesized in the presence of the primer, an agent for polymerization, and the four nucleotides described below. The product will be partially complementary to the single-stranded nucleic acid and will hybridize with the nucleic acid strand to from a duplex of unequal length strands that may then be separated into single strands, as described above, to produce two single separated complementary strands. Alternatively, two appropriate primers may be added to the single-stranded nucleic acid and the reaction is carried out.

If the original nucleic acid constitutes the sequence to be amplified, the primer extension product(s) produced will be completely complementary to the strands of the original nucleic acid and will hybridize therewith to form a duplex of equal length strands to be separated into single-stranded molecules.

When the complementary strands of the nucleic acid or acids are separated, whether the nucleic acid was originally double or single stranded, the strands are ready to be used as a template for the synthesis of additional nucleic acid strands. This synthesis can be performed using any suitable method. Preferably, a molar excess (for cloned nucleic acid, usually about 1000:1 primer:template, for the genomic nucleic acid, usually about $10^6$:1 primer:template) of the two oligonucleotide primers is added to the buffer containing the separated template strands. It is understood, however, that the amount of complementary strand may not be known if the process herein is used for diagnostic applications, so that the amount of primer relative to the amount of complementary strand cannot be determined with certainty. As a practical matter, however, the amount of primer added will generally be in molar excess over the amount of complementary strand (template) when the sequence to be amplified is contained in a mixture of complicated long-chain nucleic acid strands. A large molar excess is preferred to improve the efficiency of the process.

Conventional nucleotides, preferably dATP, dCTP, and dGTP, are added to the amplification reaction mixture in adequate amounts, i.e., approximately 200 µM/dNTP to about 400 µM/dNTP. As noted above, in a preferred embodiment, a portion of the conventional nucleotide dTTP is replaced with the unconventional nucleotide, dUTP. The percent of dTTP replaced by dUTP is up to 75%. Note, preferred embodiments provide a dUTP/dTTP mixture where the dUTP makes up between 20% to 40% of the composition. Note that dUTP amounts that exceed 75% of the dTTP fraction of dNTPs have not added to the surprising performance enhancement realized by the present invention, and in fact these high amounts of dUTP may begin to have a deleterious effect on these beneficial results, i.e., a general decrease in product formation. The resulting solution dATP, dCTP, dGTP, dUTP/dTTP, is preferably heated to a temperature from about 90° C.-95° C. for about 1 to 10 minutes, preferably from 15 sec to 2 minutes. After this heating period, the solution is allowed to cool to a temperature from about 60° C., which is preferable for the primer hybridization. The polymerase then performs nucleic acid synthesis at a temperature well above room temperature, preferably at a temperature from about 60 to 75° C. As previously noted, other conventional nucleotide/unconventional nucleotide combinations can be used in accordance with the present invention.

The newly synthesized strand and its complementary nucleic acid strand form a double-stranded molecule which is used in the succeeding steps of the process. In the next step, the strands of the double-stranded molecule are separated using any of the procedures described above to provide single-stranded molecules.

New nucleic acid is synthesized on the single-stranded molecules. Additional polymerase, nucleotides, and primers may be added if necessary for the reaction to proceed under the conditions prescribed above. Again, the synthesis will be initiated at one end of the oligonucleotide primers and will proceed along the single strands of the template to produce additional nucleic acids.

The steps of strand separation and extension product synthesis can be repeated as often as needed to produce the desired quantity of the specific nucleic acid sequence. The amount of the specific nucleic acid sequence produced will increase in an exponential fashion.

When it is desired to produce more than one specific nucleic acid sequence from the first nucleic acid or mixture of nucleic acids, the appropriate number of different oligonucleotide primers are utilized. For example, if two different specific nucleic acid sequences are to be produced, four primers are utilized. Two of the primers are specific for one of the specific nucleic acid sequences and the other two primers are specific for the second specific nucleic acid sequence. In this matter, each of the two different specific sequences can be produced exponentially by the present process. Of course in instances where nucleic acid sequences are the same, primer sequences will be the same.

The present invention can be performed in a step-wise fashion where after each step new reagents are added, or simultaneously, wherein all reagents are added at the initial step, or partially step-wise and partially simultaneously, wherein fresh reagent is added after a given number of steps. After the appropriate length of time has passed to produce the desired amount of the specific nucleic acid sequence, the reaction may be halted by inactivating the enzymes in any known manner or separating the components of the reaction.

Thus, in amplifying a nucleic acid molecule according to the present invention, the nucleic acid molecule is contacted with a composition comprising a polymerase in an appropriate reaction mix, having a dNTP mixture that includes up to 75% of the dTTP replaced with dUTP or a combination of dUTP and an unconventional nucleotide. In addition, in combination with this embodiment, appropriate primers may be designed to include uracil instead of thymidine. In another embodiment, the amplification reaction mix may have a portion of the dNTPs replaced with dUTP as described above, and the appropriate primers may be designed to include one or more uracil bases.

As such, the present invention provides modified dNTP mixes and corresponding methods using dNTP containing mixes, for limiting or reducing the formation of primer-aggregates during amplification reactions, e.g., PCR, real-time PCR, etc. In one embodiment, a portion of the dNTP mixture in the reaction mixture is replaced with dUTP, e.g., replace dTTP with dUTP. Standard concentrations of dNTPs are used as a starting point within the target reactions as is well known in the art, i.e., approximately 200 µM to 400 µM per dNTP for PCR. In one embodiment, from 10% to 75% of the dTTP in a standard dNTP mix is replaced with dUTP, and preferably from about 20% to about 40% of the dTTP in the standard dNTP mix is replaced with dUTP. Other embodiments of the present invention include the use of other unconventional nucleotides within the dNTP mix, for example dITP, deaza-dGTP, and mixtures thereof, which can be combined with the dUTP to replace from about 10% to 75% of the dTTP.

Note that the presence of unconventional nucleotides, e.g., dUTP, promote fill-in reactions to be completed with a minimum number of primer-aggregates formed. In general, inclusion of an unconventional nucleotide is less thermodynamically favorable for incorporation based on annealing temperatures used in standard PCR. Where a fill-in reaction is not required, the benefit of inclusion of an unconventional nucleotide is limited. As such, primer fill-in reactions result in primer-aggregates are reduced in number. Also note that dUTP is preferred in some embodiments where specificity is required, i.e., dUTP forms a base pair with dATP, whereas other unconventional nucleotides are non-specific and able to pair with dATP, dCTP, dGTP or dTTP. Note that prior art usage of dUTP focused on incorporation of dUTP into product (amplicon) and subsequent degradation of such product with UNG. UNG treatment was performed on PCR reactions before dUTP was added to ensure that any contaminate UTP containing product was degraded before the next reaction, thereby enhancing the reaction specificity.

In an alternative embodiment, primers are designed to exhibit uracil in place of standard dNTPs in order to reduce the thermal-dynamic favorability of primer-aggregate formation. For example, dUTP, in the context of primer-aggregate formation, will tend to form weaker interactions as compared to dTTP at the same positions. This reduction in interaction strength is relevant when the level of mispairing is high or the number of base-pair overlap is small, i.e., conditions that favor primer-dimer formation. The same dUTP containing primers have sufficient interaction strength with their target template site to remain hybridized under the proper temperature cycling PCR conditions. As such, primer design that includes dUTP incorporation selectively favors a reduction in the formation of primer-aggregates, while maintaining the relative hybridization strength of the primer with its template target site. In one embodiment of the invention, all the dTTP in the primer is replaced with dUTP.

Polyols Facilitate the PCR of Template NA Having Secondary Structure

Polyols, i.e., alcohol derivatives of monosaccharide, facilitate amplification of template nucleic acid molecules that include some level of secondary structure. In one embodiment of the invention, one or more polyol compounds is included within a standard amplification reaction to enhance the sensitivity of amplification on target template nucleic acid (NA) where the NA has some degree of secondary structure. Without being bound by theory, it is believed that the polyol acts as a chemical melting agent on the template nucleic acid, thereby facilitating amplification of the template at lower denaturation temperatures.

The present invention preferably includes one or more polyols in a reaction mixture. In particular, the present invention provides for the inclusion of polyols in amplification reactions where the target amplification sequence has increased levels of secondary structure. Illustrative polyols for use in the present invention include, but are not limited to, glycerol, sorbitol, mannitol, maltitol, arabitol, and adonitol etc. In preferred embodiments the polyol is sorbitol or mannitol, alone or in combination. Polyol concentration in amplification reactions can range from about 100 mM to about 500 mM, preferably is from about 50 mM to about 400 mM, and is most preferably from about 100 mM to about 300 mM. Inclusion of other melting or disruptive agents in combination with the polyol during amplification is anticipated, for example, inclusion of from 1% to 5% DMSO, or other like alkyl-sulfoxides, from 50 ng to about 500 ng single-stranded binding protein, from about 1% to about 5% n-propyl sulfoxide solution, from about 100 mM to 500 mM trehalose, and up to 75% replacement of the dTTP with dUTP in the dNTP mix, are all within the scope of the present invention. Note that the combination of DMSO with sorbitol has been shown to reduce non-specific amplification during amplification reactions (see U.S. Pat. No. 6,783,940, incorporated by reference herein). As presented herein, DMSO and other like alkyl-sulfoxides, combined with polyols, sugars and/or betaines can be used, with or without dUTP embodiments of the present invention, to reduce primer-aggregate formation; these same combinations also facilitate performance or amplification by increasing amplification specificity and yield. In the present invention, compositions of dUTP, alkyl-sulfoxides, polyols and sugars like trehalose, provide substantial benefit to reducing prime-aggregate and non-specific amplification products formation. Illustrative compositions and combinations of the present invention are shown in the Examples that follow.

Without being bound by theory, it is believed that the inclusion of a polyol in the reaction mixture serves at least the two-fold effect of increasing the yield of amplicon during amplification of template molecules having some level of secondary structure and of additionally maintaining the stability of the buffer during multiple cycles of freeze/thaw.

Concentrations of ingredients useful in embodiments of the high performance reaction mixtures are as shown in Table 1. Note that the preferred concentration for TAPs-KOH is 25 mM with 15 mM KCl and for the TAPs-Tris is 25 mM with 50 mM KCl, both with a final buffer pH of about 8. Embodiments using the zwitterionic buffer formulations can have one or more of AFP, carrier protein, sorbitol, mannitol, DMSO, SSBP, and a dNTP mix having a percentage of the dTTP or other dNTP replaced with a unconventional nucleotide like dUTP. Typically, the composition has a pH of between about 7.9 and 8.2 for optimal effects. Other pH can be used but with limited results.

TABLE 1

High Performance PCR Mix/Real-Time PCR Mix

| Ingredient | Useful Concentration Range (Final) | Preferred Concentration (Final) |
|---|---|---|
| Sorbitol, Trehalose, DMSO and/or mixtures thereof | 10 mM-300 mM | 100 mM |
| dNTP Mix/% dUTP in Replacement of dTTP (or other unconventional nucleotides) | dATP 100 µM-500 µM<br>dCTP 100 µM-500 µM<br>dGTP 100 µM-500 µM<br>dTTP + dUTP µM<br>dTTP/dUTP 75%:25%-25%:75% | dATP 200 µM<br>dCTP 200 µM<br>dGTP µM<br>dTTP + dUTP 200 µM<br>dTTP/dUTP 75%:25% |
| Nucleic Acid Polymerase | 0.5 to 2 Units | 2 Units |
| Mg Ion Concentration | 3 mM to 10 mM | 5 mM and 8 mM |
| Potassium Salt Concentration | 10 mM to 80 mM | 40 mM to 60 mM |
| anti-freeze protein, e.g., AFP type I, AFGP or mixtures of same//Carrier Protein | 10 µg/ml to 200 µg/ml//100 µg/ml to 300 µg/ml | 50 µg/ml/100 µg/ml |
| Buffering Ingredient, e.g., TAPS-Tris | Taps 10 mM-40 mM<br>Tris 5 mM-25 mM | Taps 25 mM<br>Tris 10.3 mM |

Any reasonable source of polyol can be used in the present invention, for example sorbitol can be obtained from Sigma/Fluka and mannitol can be obtained from Sigma/Fluka.

Compositions of High Performance Real Time PCR Buffers

The present invention further provides high performance amplification mixtures for use in amplification reactions, preferably in standard PCR and real-time PCR. Mixtures in accordance with the present invention can include sorbitol, anti-freeze protein (AFP1, AFGP, mixtures of AFP1 and AFGP), carrier protein, nucleic acid polymerase, preferably a thermophilic or hyperthermophilic polymerase, and have a modified pH, obtained through a buffer system that utilizes a zwitterionic formulation. Illustrative zwitterionic formulations include HEPES-KOH, TAPS-Tris, HEPES-Tris, HEPES-KOH, TAPS-KOH or TAPS-Tris. Preferred embodiments of the present invention utilize a system that includes TAPS-KOH and/or TAPS-Tris, and most preferably TAPS-Tris. Preferred pH ranges for these mixtures are dependent on the final use, for example, mixes for use in real-time PCR are buffered to have a pH of from about 7.9 to about 8.7, and preferably from about 8.2 to about 8.7. Note that buffers for use in standard PCR are modified to have a pH of from about 7.9 to 8.9. In preferred embodiments, the final potassium salt concentration is between 10 mM and 80 mM. The dNTP mix of the buffer system includes from about 10% to about 50% dUTPs (in replacement of dTTPs in the dNTP mix), and more preferably from about 10% to about 30% dUTPs (in replacement of dTTPs in the dNTP mix). Further, in some embodiments, DMSO, SSBP, n-propyl sulfoxide, and/or trehalose can be included in the high performance buffer.

PCR and Real-Time PCR Buffer Kits

The present invention further provides kits that include the composition embodiments of the present invention. Kits can include reaction mixtures of the invention, for example embodiments of the high performance PCR mixtures of the invention, or alternatively, pre-determined stand alone amounts of dNTP mixtures have embodiments of the dUTP/dTTP mix of the invention, which are added to PCR buffers or are combined with enzymes used in the target use, combined with the invention.

Having generally described the invention, the same will be more readily understood by reference to the following examples, which are provided by way of illustration and are not intended as limiting.

EXAMPLES

Example 1 dUTP Incorporation During Amplification Reactions Reduces Primer-Aggregate Formation Replacement of dTTP with dUTP during amplification reactions reduces primer-dimer formation where the primer has a 5' overhang. A series of PCR reactions were prepared having GADPH and SRY forward and reverse primers, GADPH and SRY probes, and appropriate plasmid templates. Each reaction either received standard dNTP mixes (10 mM of dATP, dCTP, dGTP and dTTP) or modified dNTP mixes where the dATP, dCTP and dGTP were held constant at 10 mM and some or all of the dTTP was replaced with dUTP. For example a 20% dUTP reaction contained 10 mM of dATP, 10 mM dCTP, 10 mM dGTP, 8 mM dTTP and 2 mM dUTP.

As shown in FIG. 1, primer-dimer formation is significantly reduced through inclusion of dUTP into the PCR reaction conditions. dUTP replacement seems to have a maximal effect on reducing dimer formation when approximately 50% of the dTTP is replaced with dUTP.

Figure 2A:
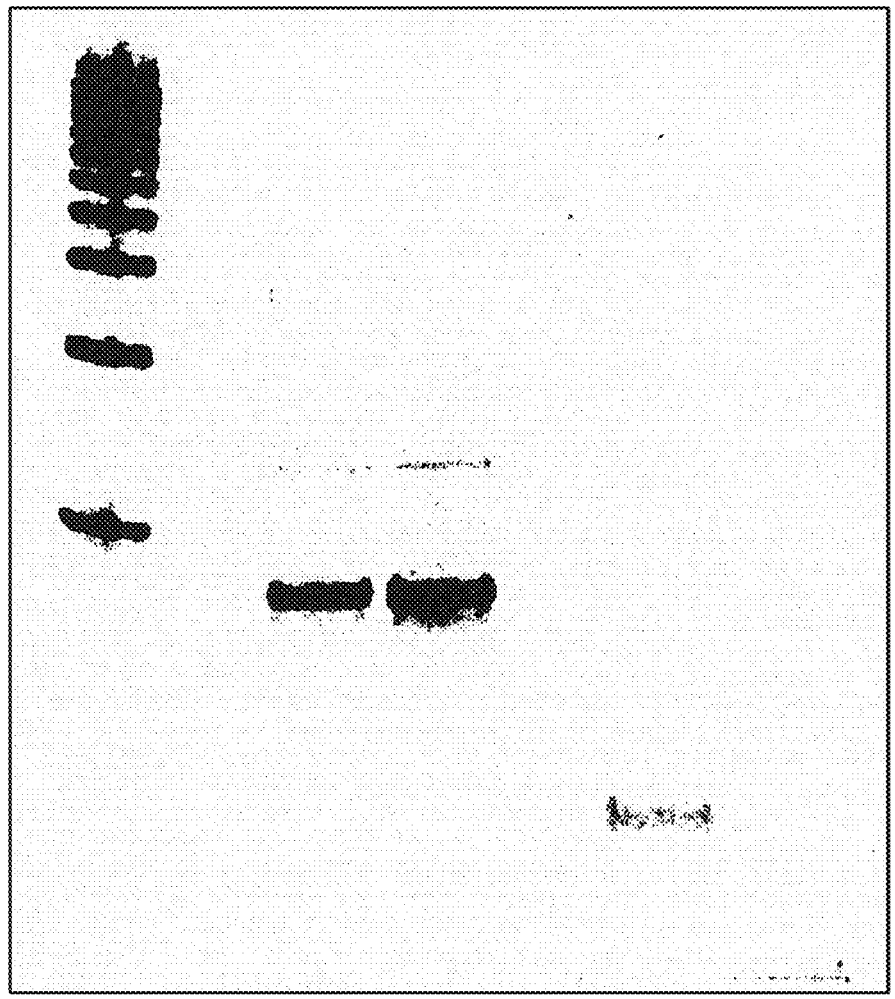
FIG. 2 is a stained 1% agarose gel showing the reaction products from PCR comparing a control reaction to a reaction where 20% of the dTTP was replaced by dUTP. Replacement of dTTP with dUTP significantly reduced the amount of primer-dimer formed during PCR.

As shown in FIG. 2, inclusion of dUTP into the PCR reaction mixture causes a dramatic decrease in primer-dimer formation. Both HotMaster Taq and NTC supported the decrease in primer-dimer formation. Tables 2 and 3 illustrate the reaction conditions used for a three step thermal cycle −95° C. for one minute—then for twenty seconds, step 2, 53° C. for twenty seconds and 68° C. for twenty seconds.

primer-dimer formation, thereby maximizing the specificity and sensitivity of the reaction conditions.

Example 2

Unconventional Nucleotides Shift the Melt Curve to Lower Temperatures

The following Example was performed to compare the effect on template melting by replacement of a percentage of the dNTPs with a unconventional nucleotide in the standard PCR buffer. Reactions were prepared as shown in Tables 4 and 5, and run with the appropriate analog as per protocol outlined in Table 6.

TABLE 4 unconventional nucleotide Mix Composition

| Analog | Standard dNTP Mix | 7-deaza-dGTP Mix | dITP Mix | dUTP Mix | dUTP/deaza Mix | dUTP/dITP | dUTP/dITP/deaza Mix |
|---|---|---|---|---|---|---|---|
| dATP | 10 mM | 10 mM | 10 mM | 10 mM | 10 mM | 10 mM | 10 mM |
| dCTP | 10 mM | 10 mM | 10 mM | 10 mM | 10 mM | 10 mM | 10 mM |
| dGTP | 10 mM | 5 mM | 5 mM | 10 mM | 5 mM | 5 mM | 5 mM |
| dTTP | 10 mM | 10 mM | 10 mM | 5 mM | 5 mM | 5 mM | 5 mM |
| dUTP | | | | 5 mM | 5 mM | 5 mM | 5 mM |
| dITP | | | 5 mM | | | 5 mM | 2.5 mM |
| 7-deaza-dGTP | | 5 mM | | | 5 mM | | 2.5 mM |

TABLE 2

HotMaster Taq Reaction With Standard dNTPs

| Reaction Component | Initial Concentration | Final Concentration Volumes |
|---|---|---|
| QuantMaster Probe Buffer | 10X | 1X |
| dATP | 10 mM | 200 μM |
| dCTP | 10 mM | 200 μM |
| dGTP | 10 mM | 200 μM |
| dTTP | 10 mM | 200 μM |
| Factor VIII Forward Primer | 10 μM | 200 nM |
| Factor VIII Reverse Primer | 10 μM | 200 nM |
| Taq Polymerase | 5 U/μL | 1 U |
| MBGW | NA | 36.8-38.8 μl |
| Humand gDNA (Promega) | 25 ng/μl | 50 ng |

TABLE 3

HotMaster Taq Reactions With dUTP Mix

| Reaction Component | Initial Concentration or Volume | Final Concentration Volume |
|---|---|---|
| QuantMaster Probe Buffer | 10X | 1X |
| dATP | 10 mM | 200 μM |
| dCTP | 10 mM | 200 μM |
| dGTP | 10 mM | 200 μM |
| dTTP | 8 mM | 160 μM |
| dUTP | 2 mM | 40 μM |
| Factor VIII ForwardPrimer | 10 μM | 200 nM |
| Factor VIII Reverse Primer | 10 μM | 200 nM |
| Taq Polymerase | 5 U/μL | 1 U |
| MBGW | NA | 36.8-38.8 μL |
| human gDNA (Promega) | 25 ng/μl | 50 ng |

The preceding Example illustrates that replacement of up-to 50% or more of the dTTP with dUTP results in a reduction in

TABLE 5

Figure 3:
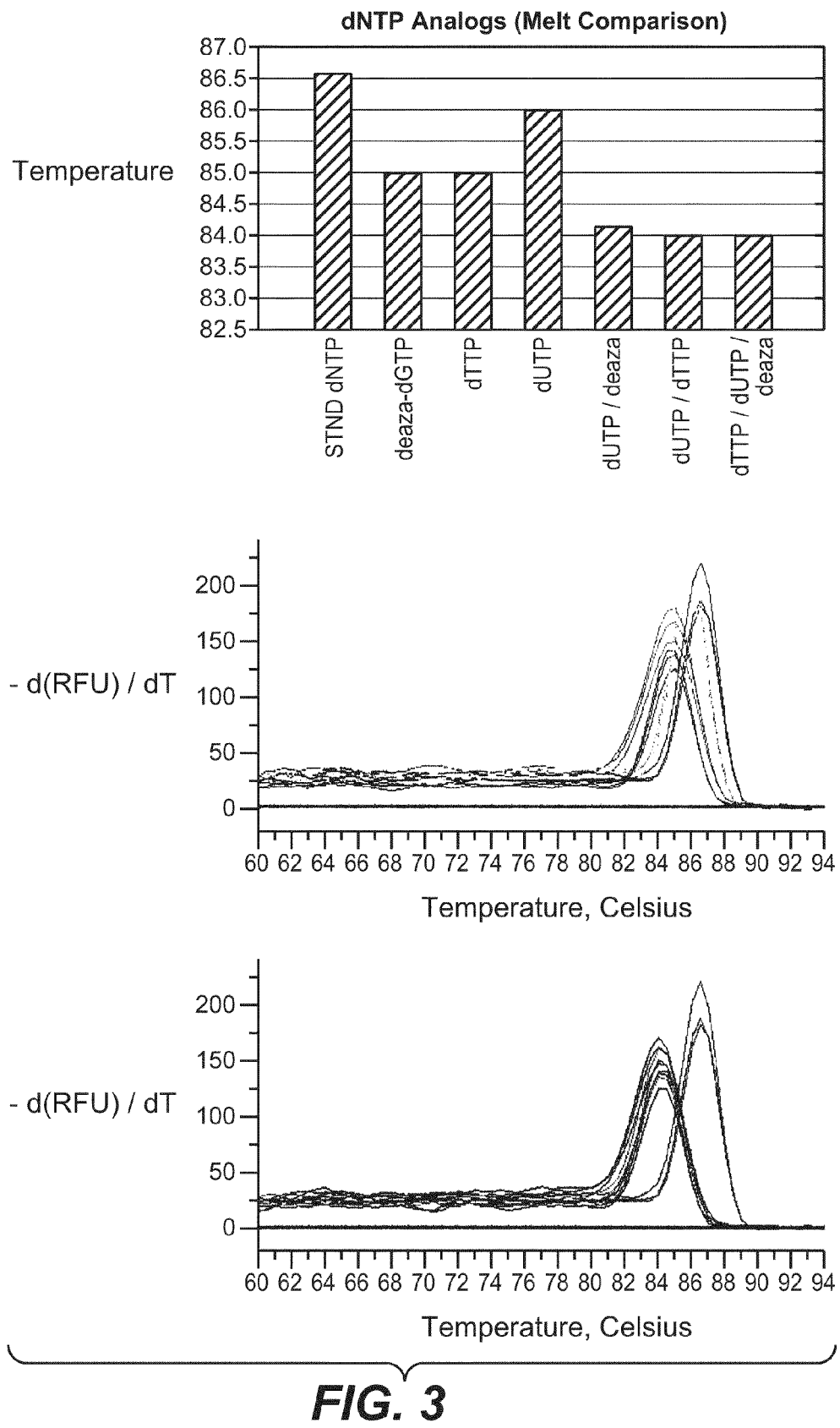
FIG. 3 graphically represents melt curve comparisons for unconventional nucleotides and mixtures.

Reaction Set-Up For FIG. 3

| Reaction Component | Final Concentration | μL/50 μL Reaction |
|---|---|---|
| 10X QuantMaster SYBR Buffer | 1X | 5 μL |
| unconventional nucleotide Mix | see Table 4 | 1.5 μL |
| TNF-A Forward Primer (10 μM) | 100 nM | 0.5 μL |
| TNF-A Reverse Primer (10 μM) | 100 nM | 0.5 μL |
| SYBR Green I (1:5K) | 1:50K | 5 μL |
| HotMaster Taq DNA Polymerase (5 U/μL) | 1 U | 0.2 μL |
| MBGW | N/A | 36.8 μL |
| Human gDNA (50 ng/μL) | 25 ng | 0.5 μL |

TABLE 6

Cycle Protocol

| Cycle Number | Temperature | Time |
|---|---|---|
| Cycle 1 | (1X) | |
| | Step 1 95.0° C. | 1:00 |
| Cycle 2 | (40X) | |
| | Step 1 95.0° C. | 0:20 |
| | Step 2 58.0° C. | 0:20 |
| | Step 3 68.0° C. | 0:20 |
| | Data collection and real-time analysis enabled | |
| Cycle 3 | (1X) | |
| | Step 1: 95° C. | 1:00 |
| Cycle 4 | (1X) | |
| | Step 1: 55.0° C. | 2:00 |

TABLE 6-continued

| Cycle Protocol | | |
|---|---|---|
| Cycle Number | Temperature | Time |
| Cycle 5 | (80X) Step 1: 55.0° C. Increase setpoint temperature after cycle 2 by 0.5° C., melt curve data collection and analysis enabled (see FIG. 3) | 0:10 |
| Cycle 6 | (1X) Step 1: 4.0° C. | Hold |

FIG. 3 illustrates that replacement of one or more standard dNTPs with a unconventional nucleotide results in a small but significant facilitation of template melting as compared to standard dNTP compositions. This data illustrates the decreased thermodynamically favorability for incorporation at primer annealing conditions.

Example 3 dUTP does not Effect Ct, RFU or Yield During Real Time-PCR

From the proceeding Examples, inclusion of dUTP for dTTP provides a significant benefit toward reducing the levels of primer-dimer formation during PCR. To determine whether the replacement of dTTP with dUTP in a standard dNTP mix adversely affected sensitivity or signal size during PCR, for example, during real time PCR, comparisons were made between reactions that had from 2.5 mM to 7.5 mM dUTP in replacement of dTTP. Reactions were as substantially described in Example 1, except that a portion of the 10 mM dTTP was replaced with either 2.5 mM dUTP or 7.5 mM dUTP.

Figure 4A:
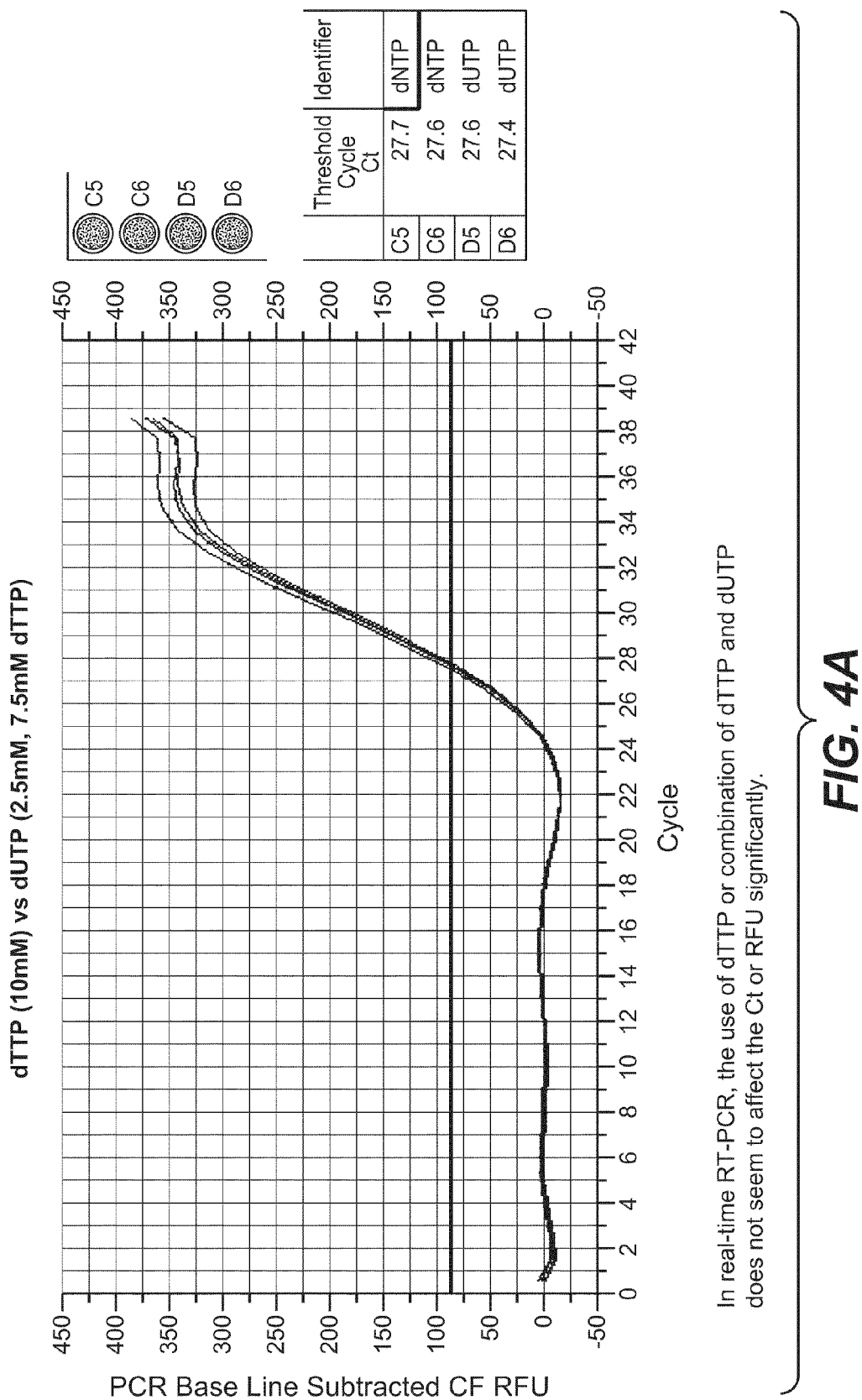
FIGS. 4A and 4B graphically illustrates that replacement of dTTP with dUTP does not significantly affect Ct or RFU during real time PCR.
Figure 4B:
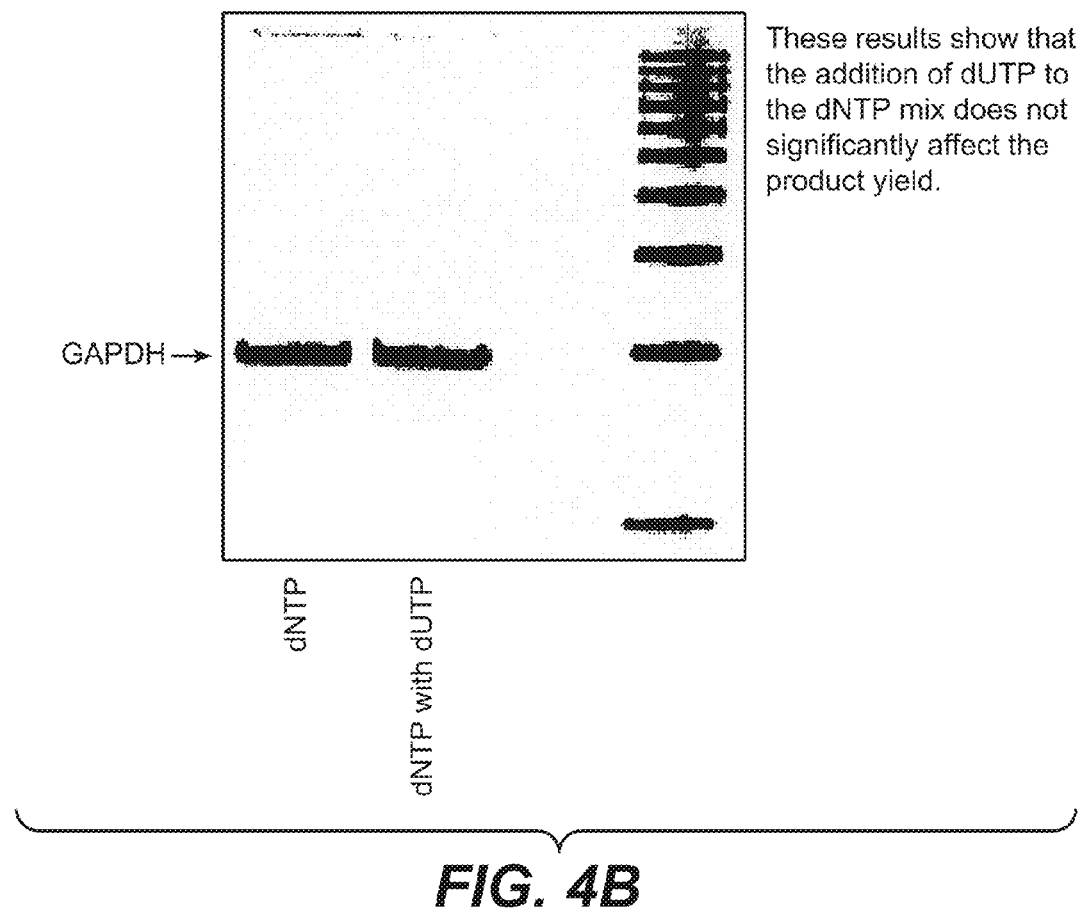

As shown in FIG. 4A, inclusion of dUTP for dTTP had little or no affect on either signal amplification or threshold cycle Ct. Further, inclusion of dUTP in the real-time PCR has little or no effect on the product yield of the reaction (see FIG. 4B).

This Example, in combination with the data shown in Examples 1 and 2, shows the utility of the present invention for providing a PCR buffer useful in reducing primer-dimer formation while maintaining yield, signal size (RFU) and Ct cycle sensitivity.

Example 4

Sorbitol in Combination with dUTP Mix Facilitates Removal of Template Secondary Structure and Enhances Amplification Performance A system was developed to investigate the effect target chemicals had on template secondary structure. As shown in FIGS. 5A and 5B, one template (derived from b-Actin) was provided within an amplification reaction, a first structure (shown schematically in 5A) having little or no secondary structure, and a second structure (shown schematically in 5B) having a significant portion of secondary structure. The second structure includes an extended region of GC rich sequence and differs from the first structure when amplified. In the absence of other factors, little or no amplification from the second structure is anticipated due to the extended region of secondary structure. Conversely, amplification from the first structure molecule results in significant product formation. Only when the secondary structure is removed with the second structure be amplified, thereby providing the product of that length.

Experiments were performed to determine the effect of target chemical agents on their ability to melt-out secondary structure from template structure number two. An increase in amplification of the second structure is indicative of the chemical agents ability to melt-out the secondary structure. Template was incubated in a standard PCR reaction with increasing amounts of sorbitol or increasing amounts of sorbitol in the presence of n-proyl-sulfoxide. Amplified products were visualized by running on an agarose gel and stained with ethidium bromide. Thermal cycling included an initial 95° C. for sixty seconds step followed by 95° C. for twenty seconds, 59° C. for twenty seconds, and 68° C. for twenty seconds repeated forty times. Tables 7 and 8 illustrate reaction conditions for FIGS. 7A, and 7B respectively:

TABLE 7

Figure 7A:
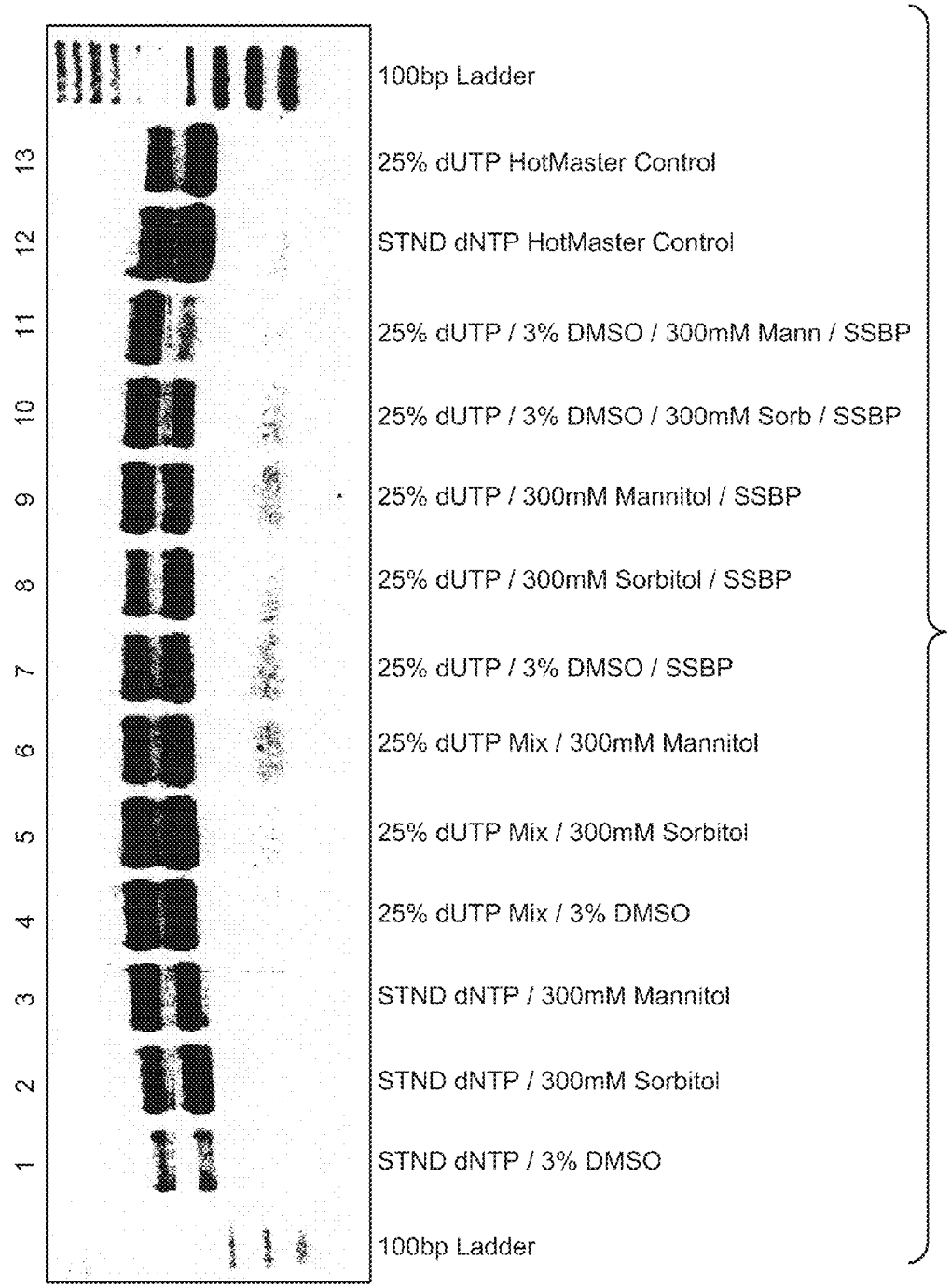

| Reaction Conditions For FIG. 7A | | | | | | | | | | | |
|---|---|---|---|---|---|---|---|---|---|---|---|
| Reaction Mixture | Reaction Component Volume | | | | | | | | | | |
| Rnx component | #1 | #2 | #3 | #4 | #5 | #6 | #7 | #8 | #9 | #10 | #11 |
| Master Mix* (µl) | 18.2 | 18.2 | 18.2 | 18.2 | 18.2 | 18.2 | 18.2 | 18.2 | 18.2 | 18.2 | 18.2 |
| 10 mM Standard dNTP Mix (µl) | 1 | 1 | 1 | | | | | | | | |
| 25% dUTP (µl) | | | | 1 | 1 | 1 | 1 | 1 | 1 | 1 | 1 |
| 99.9% DMSO (µl) | 1.5 | | | 1.5 | | | 1.5 | | | 1.5 | 1.5 |
| 1M Sorbitol (µl) | | 15 | | | 15 | | | 15 | | 15 | |
| 1M Mannitol (µl) | | | 15 | | | 15 | | | 15 | | 15 |
| SSBP (150 ng/ml) (µl) | | | | | | | 1 | 1 | 1 | 1 | 1 |
| MBGW (µl) | 29.3 | 15.8 | 15.8 | 29.3 | 15.8 | 15.8 | 28.3 | 14.8 | 14.8 | 13.3 | 13.3 |
| Total (µl) | 50 | 50 | 50 | 50 | 50 | 50 | 50 | 50 | 50 | 50 | 50 |

Buffer, 100 nM forward and reverse β-Actin Primer, 1 U Taq polymerase, and 50 ng gDNA

TABLE 8

Reaction Conditions For FIG. 7B

General Master Mix

| Reaction Component | Initial Concentration | Final Concentration | Volume |
|---|---|---|---|
| QuantMaster Probe Buffer | 10X | 1X | |
| dNTP Mix | | | |
| dATP | 10 mM | 200 μM | |
| dCTP | 10 mM | 200 μM | |
| dGTP | 10 mM | 200 μM | |
| dTTP | 7.5 mM | 150 μM | |
| dUTP | 2.5 mM | 50 μM | |
| β-Actin Forward Primer | 10 μM | 200 nM | |
| β-Actin Reverse Primer | 10 μM | 200 nM | |
| SSBP | 150 ng/μl | 150 ng | |
| Taq Polymerase | 5 U/μl | 2 U | |
| MBGW | NA | 10 μl | |
| gDNA | 25 ng/μl | 50 ng | |

| Reaction Component | 0 mM Sorbitol | 10 mM Sorbitol | 40 mM Sorbitol | 100 mM Sorbitol | 200 mM Sorbitol | 300 mM Sorbitol |
|---|---|---|---|---|---|---|
| Samples Containing No Trehalose | | | | | | |
| MBGW/50 μl reaction | 30 | 29.5 | 28 | 25 | 20 | 15 |
| 1M Sorbitol | 0 | 0.5 | 2 | 5 | 10 | 15 |
| Samples Containing 300 mM Trehalose | | | | | | |
| MBGW | 25 | 25 | 25 | 25 | 25 | 25 |
| 1M Sorbitol/Tehalose Mixture | 5 | 5 | 5 | 5 | 5 | 5 |

HotMaster Control Reactions

| Reaction Component | Initial Concentration | Final Concentration |
|---|---|---|
| HotMaster Buffer | 10X | 1X |
| Standard dNTP Mix | 10 mM Each | 200 μM each |
| β-Actin Forward Primer | 10 μM | 200 nM |
| β-Actin Reverse Primer | 10 μM | 200 nM |
| SSBP | 150 ng/μl | 150 ng |
| HotMaster Taq Polymerase | 5 U/μl | 2 U |
| MBGW | NA | 10 μl |
| gDNA | 25 ng/μl | 50 ng |

Figure 6:
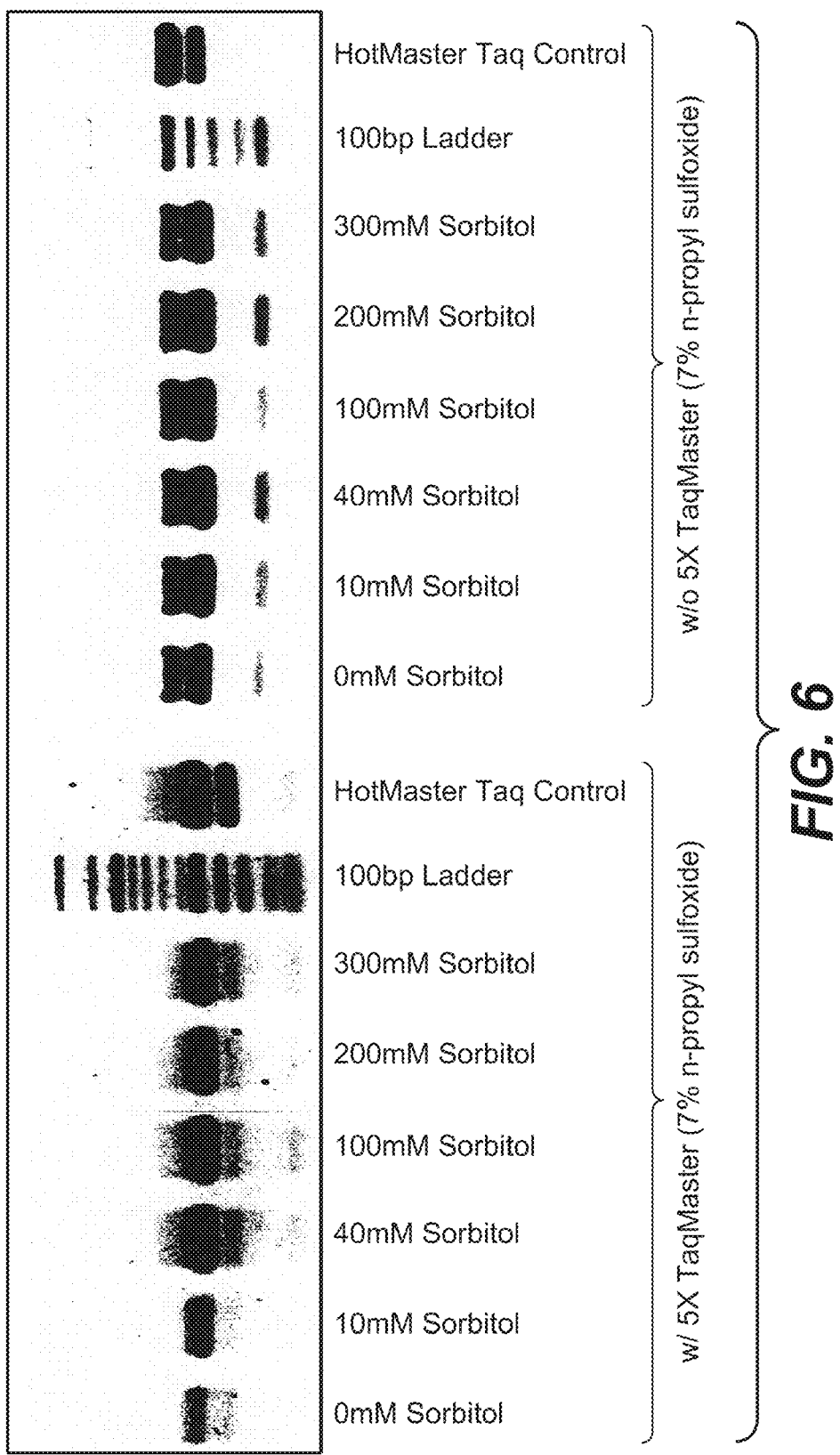
FIG. 6 is a stained 1% agarose gel showing the reaction products from PCR on the templates of FIGS. 5A and 5B in the presence of increasing amounts of sorbitol. The upper band is amplified product from the secondary structure containing molecule, indicating melting of the secondary structure, and the lower band is amplified product from the non-secondary structure containing molecule, indicating a control level of amplification of the non-secondary structure containing template.

FIGS. 6, 7A, and 7B illustrate that sorbitol alone or in combination with other agents, for example n-propyl sulfoxide, dNTP mixes containing dUTP, mannitol and single-stranded binding protein facilitated the amplification of the longer, often GC rich, template by reducing the amount of secondary structure within the template. Note that combinations of increasing amounts of sorbitol and 7% n-propyl sulfoxide (FIG. 6) was particularly effective in melting out the secondary structure and allowing for amplification of the longer template. Note also that increasing amounts of sorbitol in the presence of trehalose (right panel of FIG. 7B) caused a preferential amplification of the larger, secondary structure containing, plasmid.

The preceding Example illustrates the utility of including sorbitol alone or in combination with trehalose, n-propyl sulfoxide, dNTP mixes containing dUTP, DMSO, mannitol and SSBP, for amplification of template DNA, and in particular, template DNA high in secondary structure.

Example 5

Akyl-Sulfoxides in Combination with Trehalose Facilitate the Amplification of GC-Rich Nucleic Acid The following Example illustrates that combinations of different alkyl-sulfoxides, e.g., DMSO, N-propylsulfoxid, thtramethylenesulfoxid, with trehalose or other like sugars, facilitates amplification and reduces primer-aggregation, of nucleic acid molecules, and in particular GC-rich nucleic acid molecules.

Experiments were conducted in buffer combinations that contain the following: 1× Tuning buffer with 2.5 mM $Mg^{2+}$, Tuning buffer with 1× TaqMaster PCR Enhance, TaqMaster with N-propylsulfoxide (0.5% to 1.75%), TaqMaster with tetramethylenesulfoxide (0.015%-0.4%), TaqMaster with DMSO (2%), Glycylbetaine (Q solution) ca IM final solution, and GC-Melt (Clontech) ca 0.5 M final. All reaction were performed using Eppendorf Taq DNA polymerase. Amplification reactions were performed on a 483 bp GC-rich β-actin fragment from 50 ng human genomic DNA (Promega) in a 50 μl reaction using 1.5 U Taq in 35 cycles (5 min. 95° C.; then 35× [20 seconds at 94° C., ten seconds at 59° C. and twenty seconds at 72° C.), all reactions having been carried out in a 1× Tuning buffer with 2.5 mM $Mg(Oac)_2$ final concentration.

Note that each reaction included the following components calculated for 20 reactions: 100 μl 10× Tuning Buffer with 25 mM $Mg^{2+}$, 20 μl 10 mM dNTP mix, 20 μl β-actin forward and reverse primers (10 μM), 20 μl human gDNA (50 ng/μl), 6 μl Taq DNA polymerase (5 U/μl), and 614 MBGW $H_2O$. Approximately 40 μl of this combination was used in each 50 μl reaction. The remaining 10 μl volume was made up of the different combinations of alkyl-sulfoxides and trehalose, etcetera. or water alone.

Figure 8:
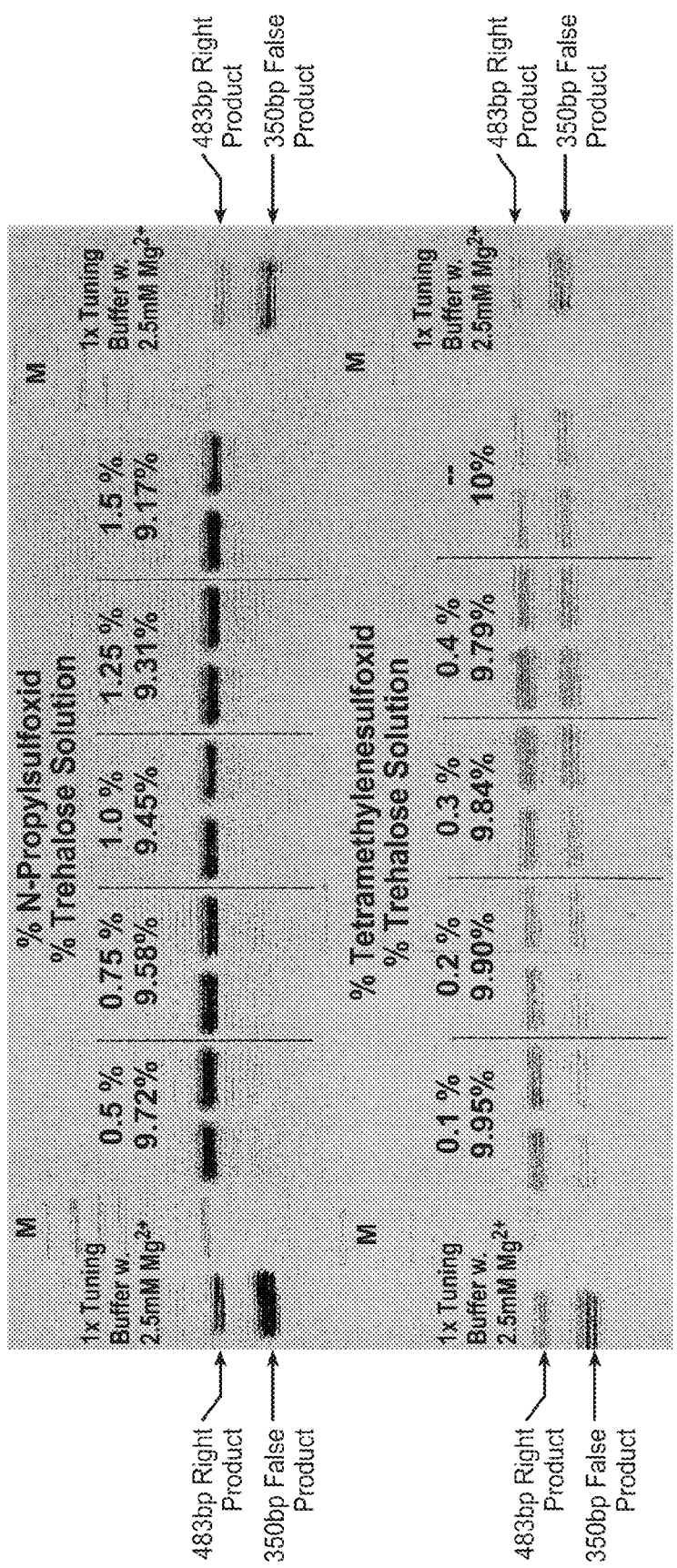
FIG. 8 is a stained agarose gel showing the reaction products from PCR comparing reactions supplemented with N-propylsulfoxid and trehalose or tetramethylene sulfoxid and trehalose.
Figure 9:
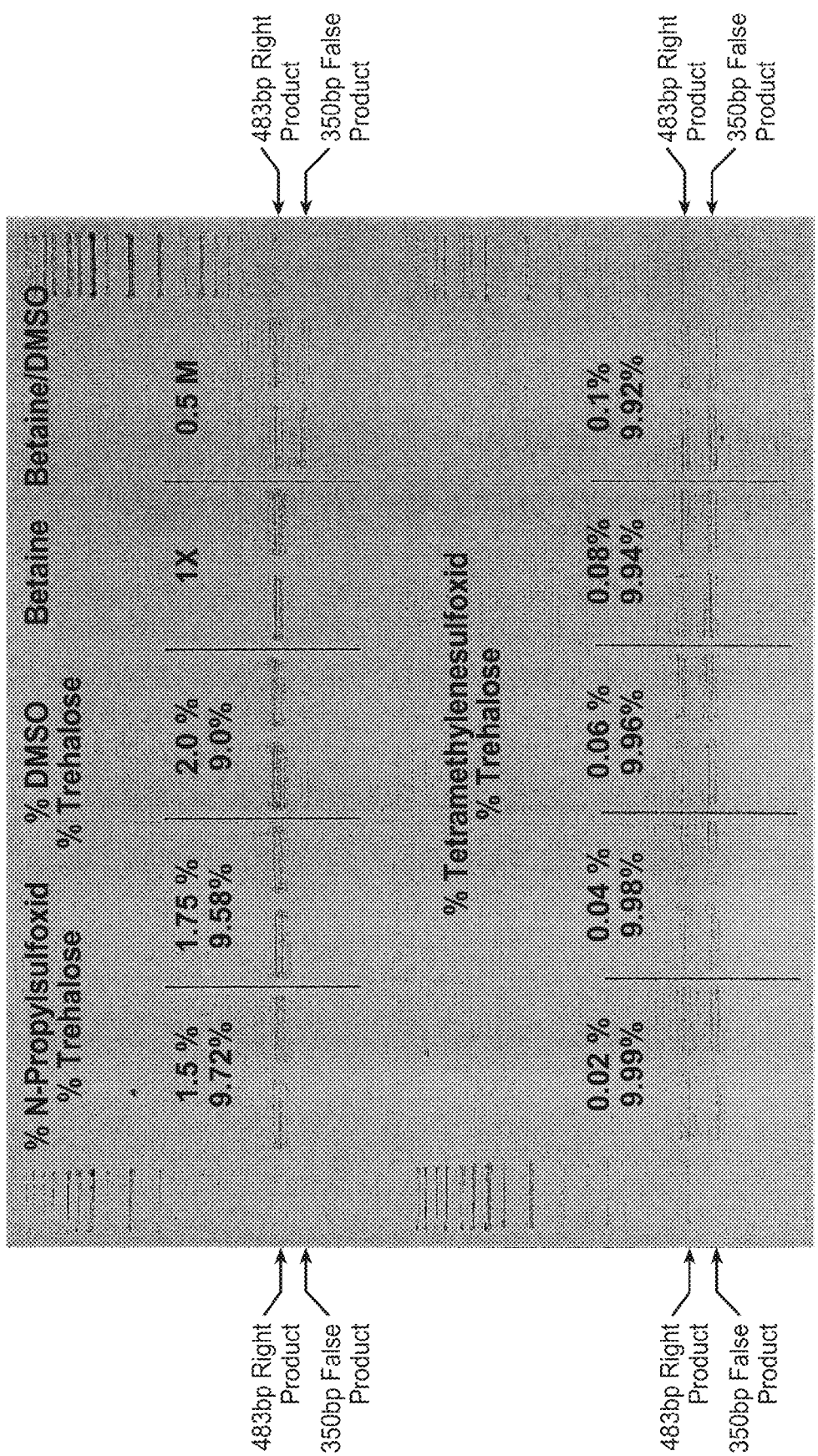
FIG. 9 is a stained agarose gel showing the reaction products from PCR comparing reactions supplemented with N-propylsulfoxid and trehalose, DMSO and trehalose and betaine.

As shown in FIGS. 8 and 9, titration of N-propylsulfoxide with trehalose facilitated amplification of difficult GC-rich target sites on gDNA. The combination of N-propylsulfoxide with trehalose outperformed the Q-solution/betaine from Qiagen (higher specific product yield at lower concentration) and GC-Melt from Clontech (better yield and specificity). Note that Clontech and Q-solution were performed to the manufacturers specification. Tetramethylene-sulfoxide was less effective than N-propylsulfoxide in these experiments for facilitating the target nucleic acid molecules.

This Example illustrates the utility of combining an alkyl-sulfoxide with a sugar like trehalose for improving amplification yield and reducing non-specific amplification. It envisioned that these combinations could be used with a polyol or dUTP embodiments as described above.

The invention has been described with reference to specific examples. These examples are not meant to limit the invention in any way. It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to patents, patent applications, and publications, each is hereby incorporated by reference for all purposes.

What is claimed is:

1. A reaction mixture for primer-based amplification and detection of a target nucleic acid, the reaction mixture comprising:
   each conventional nucleotide dATP, dCTP, and dGTP, and a combination of unconjugated dUTP and dTTP in an amount equivalent to the concentrations of dATP, dCTP and dGTP, wherein said unconjugated dUTP replaces from about 10% to about 75% of said dTTP in said combination; and at least one of a fluorescent probe, beacon or intercalating dye;
   wherein the inclusion of unconjugated dUTP reduces the formation of primer aggregates during the amplification reaction in comparison with an amplification reaction employing only conventional nucleotides; and
   wherein said reaction mixture lacks a uracil degradation enzyme.

2. The reaction mixture according to claim 1, wherein the unconjugated dUTP replaces from about 10 to about 30% of the dTTP in said combination.

3. The reaction mixture according to claim 1, wherein the unconjugated dUTP replaces from about 20 to about 40% of the dTTP in said combination.

4. The reaction mixture according to claim 1, further comprising at least one additional unconventional nucleotide, wherein the combined concentration of said unconjugated dUTP and said at least one unconventional nucleotide does not exceed 75% of any one conventional nucleotide in said reaction mixture.

5. The reaction mixture according to claim 1, wherein said reaction mixture comprises a primer pair and wherein each member of the primer pair has at least one or more uracil bases incorporated therein.

6. The reaction mixture according to claim 5, wherein each member of the primer pair has all of its thymidine bases replaced with uracil bases.

7. The reaction mixture according to claim 1, wherein the unconjugated dUTP does not exceed a final amplification reaction concentration of about 300 μM.

8. The reaction mixture according to claim 1, wherein the unconjugated dUTP does not exceed a final amplification reaction concentration of about 100 μM.

9. The reaction mixture according to claim 1, further comprising at least one polymerase enzyme.

10. The reaction mixture according to claim 1, further comprising a buffer system.

11. The reaction mixture according to claim 1, wherein the reaction mixture further comprises sorbitol or mannitol.

12. The reaction mixture according to claim 11, wherein the reaction mixture comprises 100 to 500 mM sorbitol or 100 to 200 mM mannitol.

13. A method for reducing primer aggregation during amplification and detection of target nucleic acid, the method comprising:
combining a target nucleic acid with a reaction mixture comprising each conventional nucleotide dATP, dCTP, and dGTP and a combination of dTTP with unconjugated dUTP in an amount equivalent to the concentrations of dATP, dCTP, and dGTP; wherein said unconjugated dUTP replaces from about 10% to about 75% of said dTTP in said combination;
amplifying the target nucleic acid to produce amplicons; and
detecting the amplicons so produced;
wherein the level of primer aggregate formed during the amplification step is reduced as compared to amplifying the target nucleic acid using a dNTP mix having only conventional nucleotides, wherein said method lacks an enzyme degradation step to degrade uracil-containing amplicons, and wherein said nucleic acid is DNA.

14. The method according to claim 13, wherein the reaction mixture further comprises sorbitol or mannitol.

15. The method according to claim 14, wherein the target nucleic acid has secondary structure.

16. The method according to claim 14, wherein the reaction mixture comprises 100 to 500 mM sorbitol or 100 to 300 mM mannitol.

17. The method according to claim 13, wherein the unconjugated dUTP replaces from about 10 to about 30% of the dUTP in said combination.

18. The method according to claim 13, wherein the unconjugated dUTP replaces from about 20 to about 40% of the dTTP in said combination.

19. The method according to claim 13, further comprising at least one additional unconventional nucleotide, wherein the combined concentration of said unconjugated dUTP and said at least one unconventional nucleotide does not exceed 75% of any one conventional nucleotide in said reaction mixture.

20. The method according to claim 13, wherein the unconjugated dUTP does not exceed a final amplification reaction concentration of about 300 μm.

21. The method according to claim 13, wherein the unconjugated dUTP does not exceed a final amplification concentration of about 100 μM.

22. The method according to claim 13, further comprising at least one polymerase enzyme.

23. The method according to claim 13, further comprising a buffer system.

24. The method according to claim 13, wherein said amplifying step comprises heating said target nucleic acid to a temperature greater than 60° C.

* * * * *

SEQUENCE LISTING

<160> NUMBER OF SEQ ID NOS: 2

<210> SEQ ID NO 1
<211> LENGTH: 363
<212> TYPE: DNA
<213> ORGANISM: Homo sapiens

<400> SEQUENCE: 1

| atggatgatg | atatcgccgc | gctcgtcgtc | gacaacggct | ccggcatgtg | caaggccggc | 60 |
| ttcgcgggcg | acgatgcccc | ccgggccgtc | ttcccctcca | tcgtggggcg | ccccaggcac | 120 |
| cagggcgtga | tggtgggcat | gggtcagaag | gattcctatg | tgggcgacga | ggcccagagc | 180 |
| aagagaggca | tcctcaccct | gaagtacccc | atcgagcacg | gcatcgtcac | caactgggac | 240 |
| gacatggaga | aaatctggca | ccacaccttc | tacaatgagc | tgcgtgtggc | tcccgaggag | 300 |
| cacccegtgc | tgctgaccga | ggccccectg | aacccaagg | gccaaccgcg | agaagatgac | 360 |
| cca | | | | | | 363 |

<210> SEQ ID NO 2
<211> LENGTH: 495
<212> TYPE: DNA
<213> ORGANISM: Homo sapiens

<400> SEQUENCE: 2

| atggatgatg | atatcgccgc | gctcgtcgtc | gacaacggct | ccggcatgtg | caaggccggc | 60 |
| ttcgcgggcg | acgatgcccc | ccgggccgtc | ttcccctcca | tcgtggggcg | ccccaggcac | 120 |
| caggtagggg | agctggctgg | gtggggcagc | cccgggagcg | ggcgggaggc | aagggcgctt | 180 |
| tctctgcaca | ggagcctccc | ggtttccggg | gtgggctgcg | cccgtgctca | gggcttcttg | 240 |
| tcctttcctt | cccagggcgt | gatggtgggc | atgggtcaga | aggattccta | tgtgggcgac | 300 |
| gaggcccaga | gcaagagagg | catcctcacc | ctgaagtacc | ccatcgagca | cggcatcgtc | 360 |
| accaactggg | acgacatgga | gaaaatctgg | caccacacct | tctacaatga | gctgcgtgtg | 420 |
| gctcccgagg | agcaccccgt | gctgctgacc | gaggccccccc | tgaacccca | gggccaaccg | 480 |
| cgagaagatg | accca | | | | | 495 |